United States Patent
Palm et al.

(10) Patent No.: US 11,662,487 B1
(45) Date of Patent: May 30, 2023

(54) GAMMA RAY DETECTION SYSTEM AND CALIBRATION METHOD THEREOF

(71) Applicant: TERAPET SA, Satigny (CH)

(72) Inventors: Marcus Palm, Arzier-Le Muids (CH); Christina Vallgren, Arzier-Le Muids (CH)

(73) Assignee: TERAPET SA, Satigny (CH)

( * ) Notice: Subject to any disclaimer, the term of this patent is extended or adjusted under 35 U.S.C. 154(b) by 0 days.

(21) Appl. No.: 17/919,475

(22) PCT Filed: Apr. 14, 2021

(86) PCT No.: PCT/EP2021/059665
§ 371 (c)(1),
(2) Date: Oct. 17, 2022

(87) PCT Pub. No.: WO2021/209501
PCT Pub. Date: Oct. 21, 2021

(30) Foreign Application Priority Data

Apr. 17, 2020 (EP) .................................... 20170017

(51) Int. Cl.
*G01T 7/00* (2006.01)
*A61N 5/10* (2006.01)
*G01T 1/20* (2006.01)

(52) U.S. Cl.
CPC ............ *G01T 7/005* (2013.01); *A61N 5/1071* (2013.01); *G01T 1/20181* (2020.05); *A61N 2005/1087* (2013.01)

(58) Field of Classification Search
CPC ................ G01T 7/005; G01T 1/20181; A61N 5/1071; A61N 2005/1087
See application file for complete search history.

(56) References Cited

U.S. PATENT DOCUMENTS

| | | |
|---|---|---|
| 8,809,793 B2 | 8/2014 | Wagadarikar et al. |
| 9,958,559 B1 | 5/2018 | Feng et al. |

(Continued)

FOREIGN PATENT DOCUMENTS

| | | |
|---|---|---|
| JP | 6497803 | 4/2019 |
| WO | 2017/077164 | 5/2017 |

(Continued)

OTHER PUBLICATIONS

International Search Report and Written Opinion of the ISA for PCT/EP2021/059665, dated Jul. 7, 2021, 15 pages.

(Continued)

*Primary Examiner* — Marcus H Taningco
(74) *Attorney, Agent, or Firm* — Nixon & Vanderhye P.C.

(57) ABSTRACT

Gamma ray detection system (10) comprising a computation system including a signal processing and control system (30), a detection module assembly (13) including at least one detection module (14) configured for detecting gamma ray emissions from a target zone (4), each detection module comprising at least one scintillator plate (16) having a major surface (40a) oriented to generally face the target zone and lateral minor surfaces (40b) defining edges of the scintillator layer, and a plurality of photon detectors coupled to said at least one scintillator plate and connected to the signal processing and control system. The scintillator plate comprises a material having isotopes intrinsically emitting radiation causing intrinsic scintillation events in one or more scintillator plates having an intensity measurable by the photon detectors. The gamma ray detection system comprises a calibration module configured to execute a spatial calibration procedure based on measurements of a plurality of said intrinsic scintillation events output (37) by the photon detectors, the spatial calibration procedure for determining spatial positions of scintillating events in the scin- (Continued)

tillator plate as a function of the outputs of the photon detectors.

28 Claims, 16 Drawing Sheets

(56) References Cited

U.S. PATENT DOCUMENTS

| | | | | |
|---|---|---|---|---|
| 10,274,610 | B2* | 4/2019 | Nelson | G01T 1/2002 |
| 10,393,895 | B2 | 8/2019 | Espana Palomares | |
| 2008/0067390 | A1* | 3/2008 | Ramsden | G01T 1/203 |
| | | | | 250/361 R |
| 2008/0251709 | A1 | 10/2008 | Cooke et al. | |
| 2008/0253507 | A1* | 10/2008 | Levene | G01T 1/2018 |
| | | | | 378/19 |
| 2010/0102215 | A1* | 4/2010 | Liang | G01T 1/00 |
| | | | | 250/252.1 |
| 2015/0185335 | A1* | 7/2015 | Zhao | G01T 1/2002 |
| | | | | 250/361 R |
| 2015/0276953 | A1 | 10/2015 | Espana Palomares | |
| 2016/0084974 | A1* | 3/2016 | Lerche | G01T 1/1642 |
| | | | | 250/362 |

FOREIGN PATENT DOCUMENTS

| | | |
|---|---|---|
| WO | 2018/081404 | 5/2018 |
| WO | 2019/183594 | 9/2019 |

OTHER PUBLICATIONS

International Preliminary Report on Patentability with Amended Sheets, dated Feb. 10, 2022, 2 pages.

Alva-Sanchez, 2018: H. Alva-Sánchez et.al, Understanding the intrinsic radioactivity energy spectrum from $^{176}$Lu in LYSO/LSO scintillation crystals, Scientific Report 8, Art 17310 (2018).

Afanaciev, 2015: Afanaciev, K.G., Artikov, A.M., Baranov, V.Y. et al. Response of LYSO:Ce scintillation crystals to low energy gamma-rays. Phys. Part. Nuclei Lett. 12, 319-324 (2015). https://doi.org/10.1134/S1547477115020028.

Kohonen, 1982: Kohonen, T. Self-organized formation of topologically correct feature maps. Biol. Cybern. 43, 59-69 (1982). https://doi.org/10.1007/BF00337288.

Berger, 2005: Berger, M.J., Coursey, U.S., Zucker, M.A., and Chang, J. (2005), ESTAR, PSTAR, and ASTAR: Computer Programs for Calculating Stopping-Power and Range Tables for Electrons, Protons, and Helium Ions (version 2.0.1). [Online] Available: http://physics.nist.gov/Star. National Institute of Standards and Technology, Gaithersburg, MD [accessed Jan. 31, 2020].

Delzanno, 2008: G. L. Delzanno et.al, An optimal robust equidistribution method for two-dimensional grid adaptation based on Monge-Kantorovich optimization, Journal of Computational Physics 227 (2008) 9841-9864. https://doi.org/10.1016/j.jcp.2008.07.020.

Kohonen's Self-Organizing Map description—https://en.wikipedia.org/wiki/Self-organizing_map.

* cited by examiner

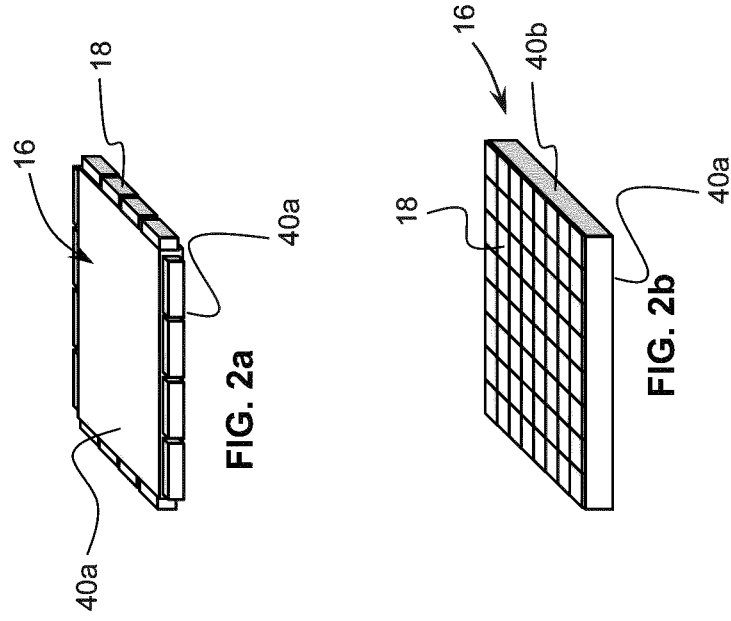
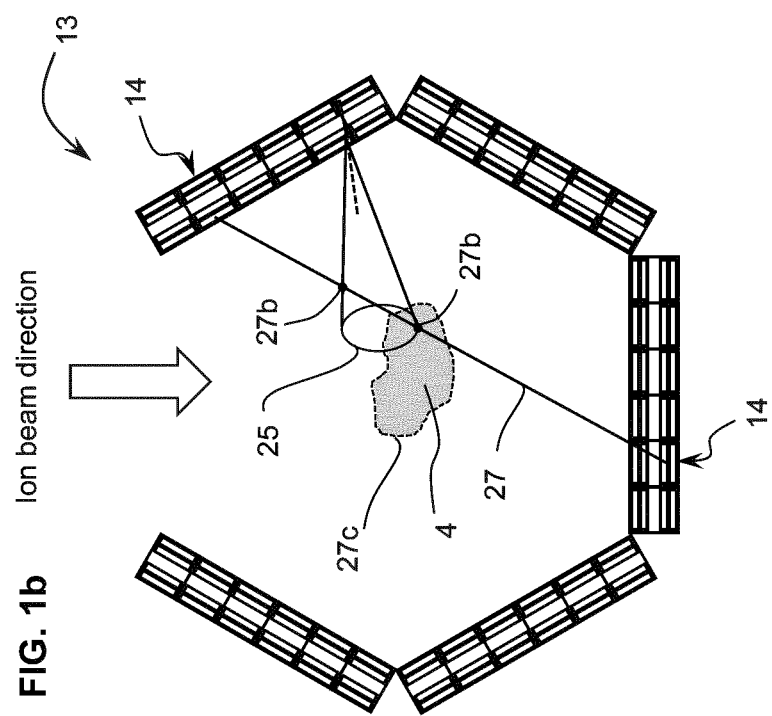

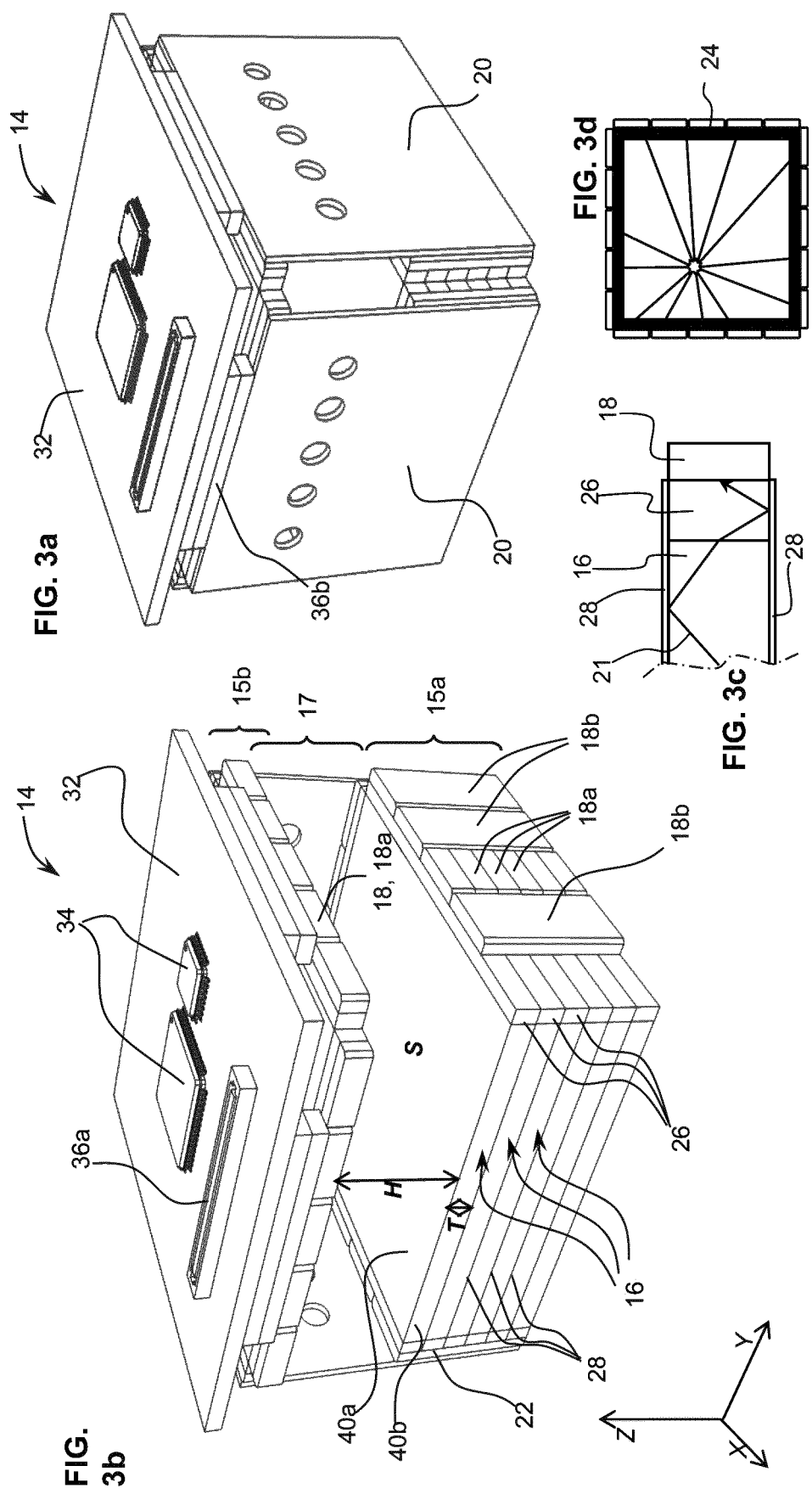

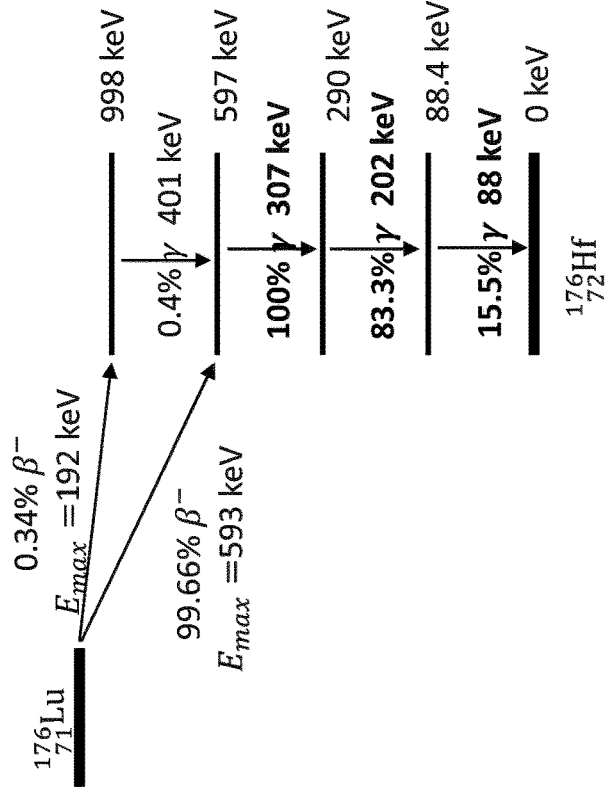
FIG. 4  176-Lutetium decay
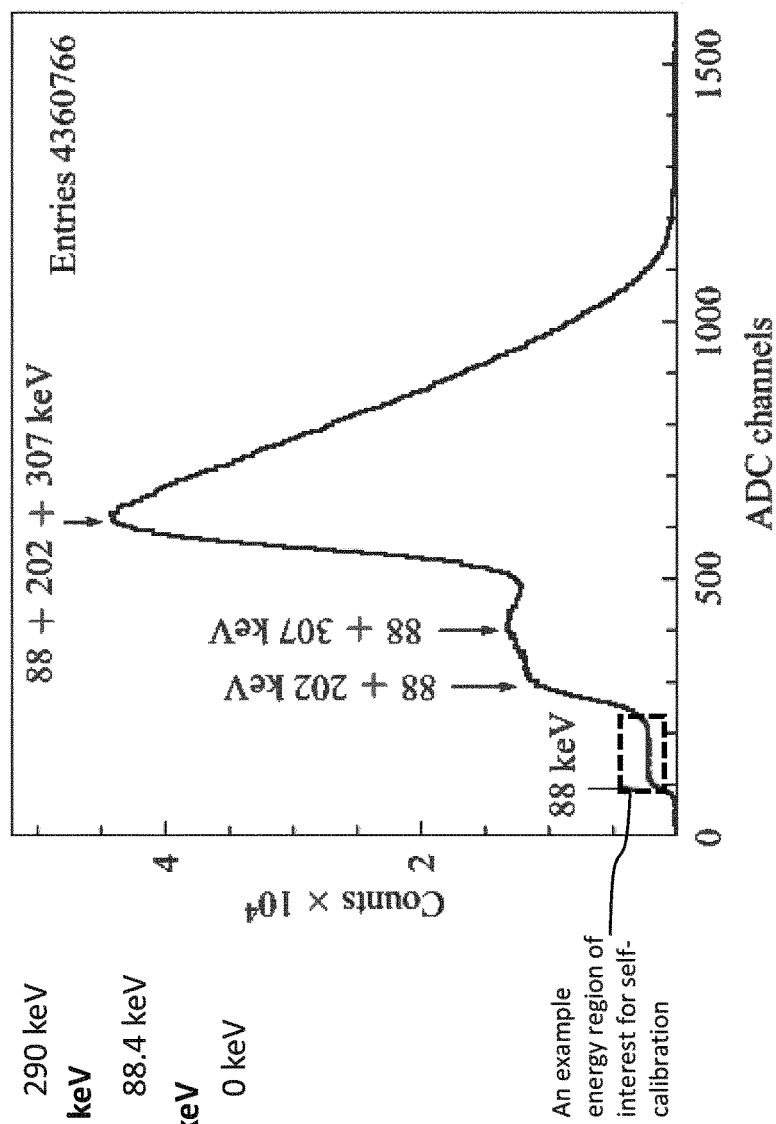
FIG. 5

Mean photon detector response maps after 25 iterations (node grid 8x8)

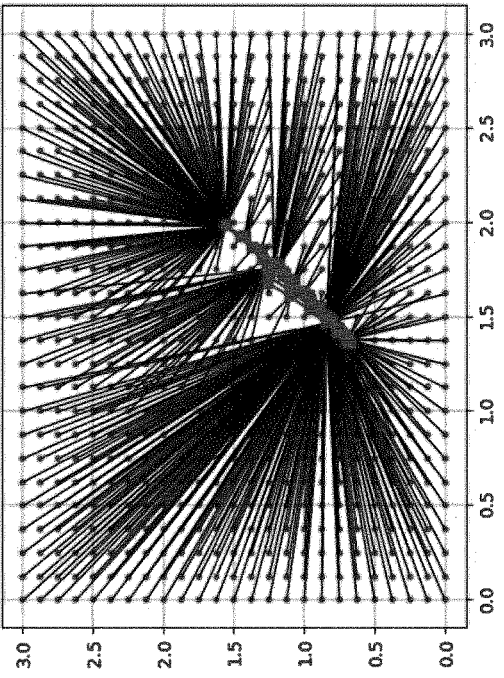
FIG. 18b Iteration 4
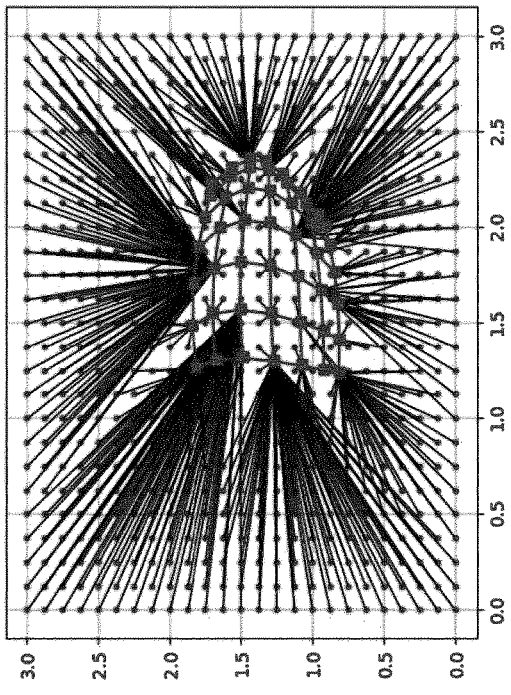
FIG. 18d Iteration 60
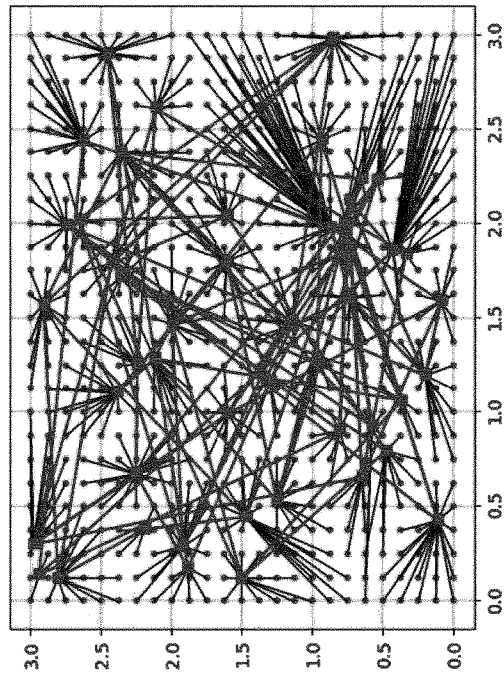
FIG. 18a Iteration 0
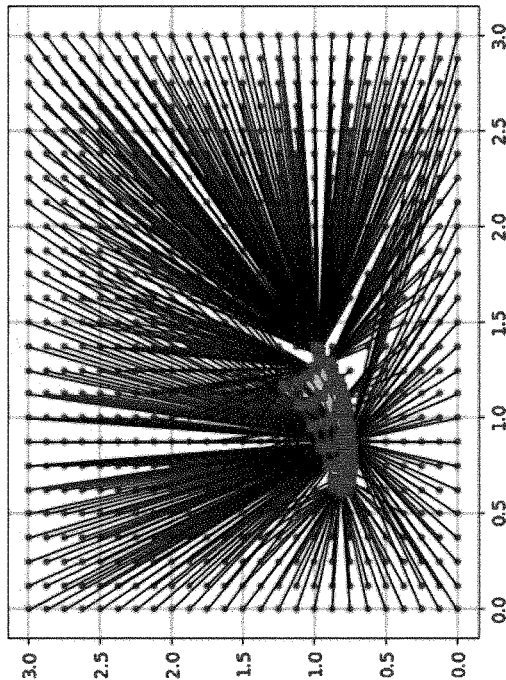
FIG. 18c Iteration 16

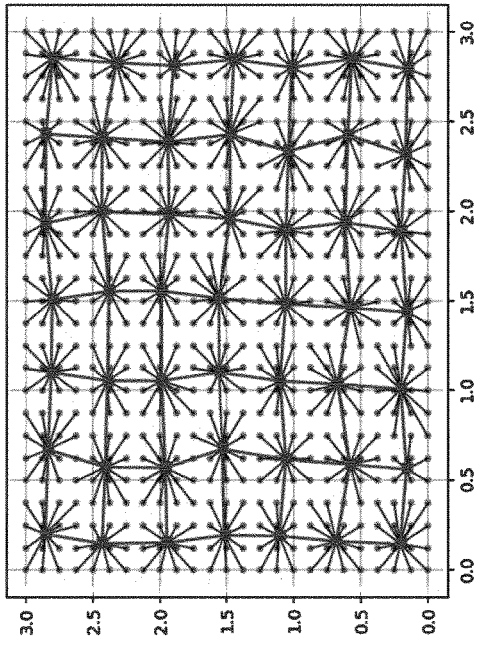
FIG. 18f Iteration 490
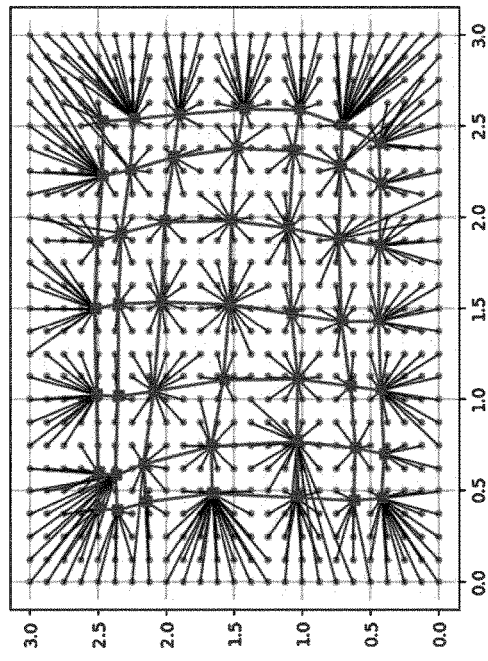
FIG. 18e Iteration 140
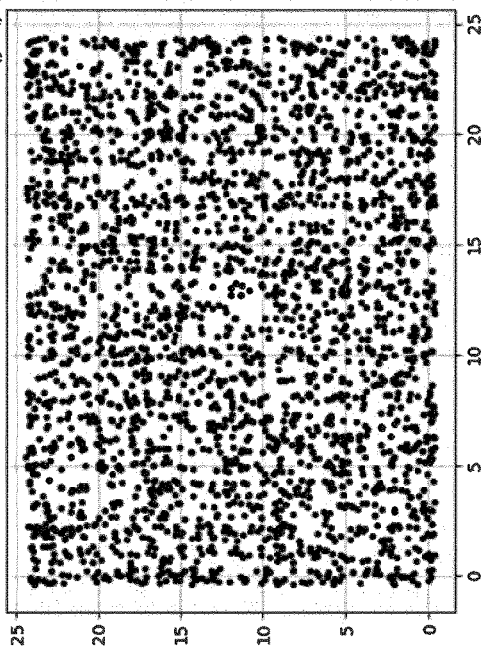
FIG. 19b Iteration = 300  With density correction ($f(\rho) = \rho^4$)
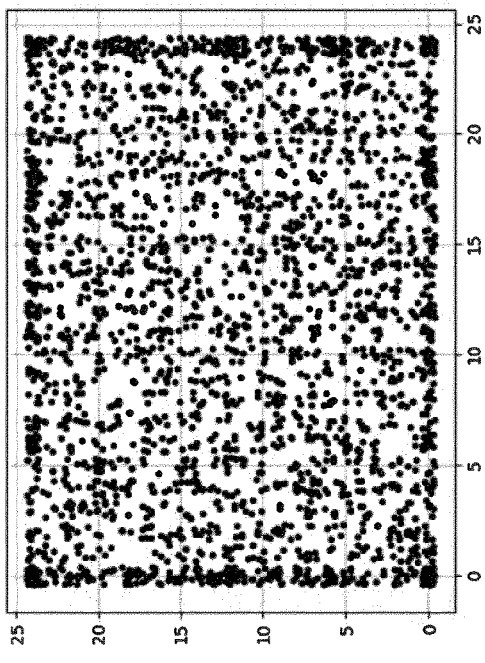
FIG. 19a Iteration = 300  No density correction

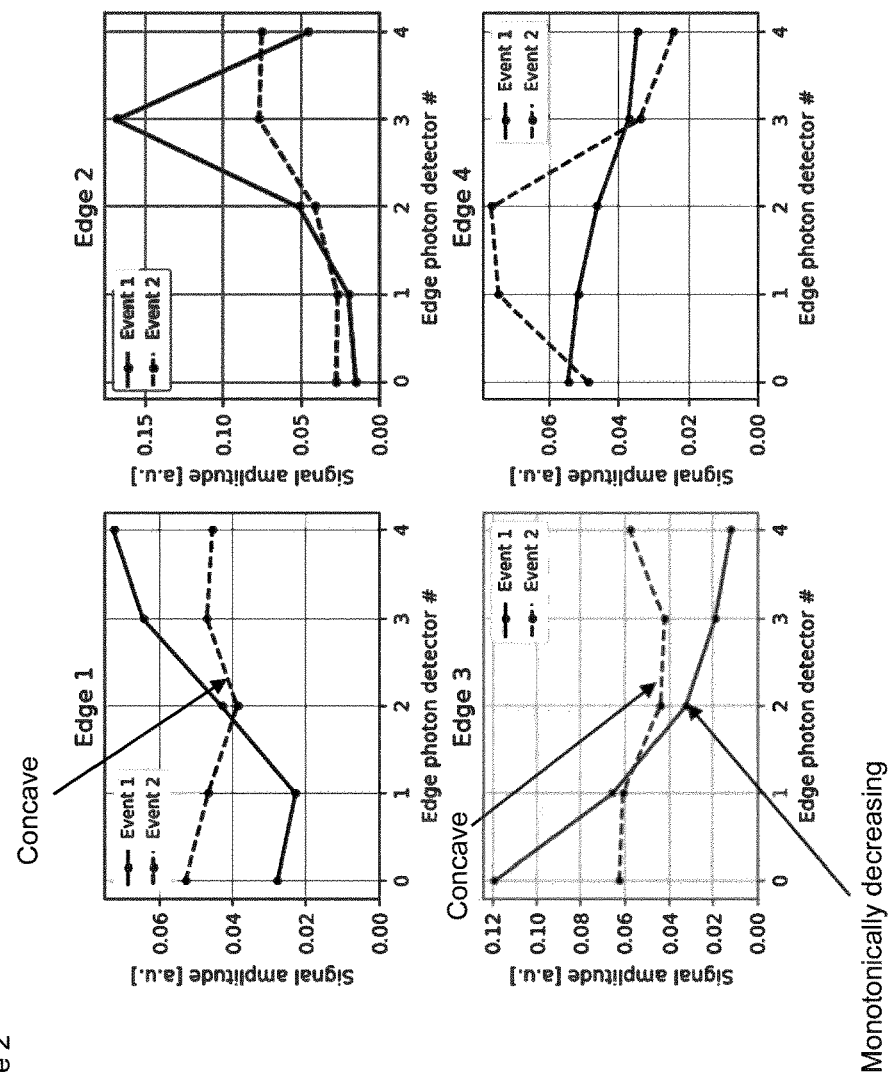
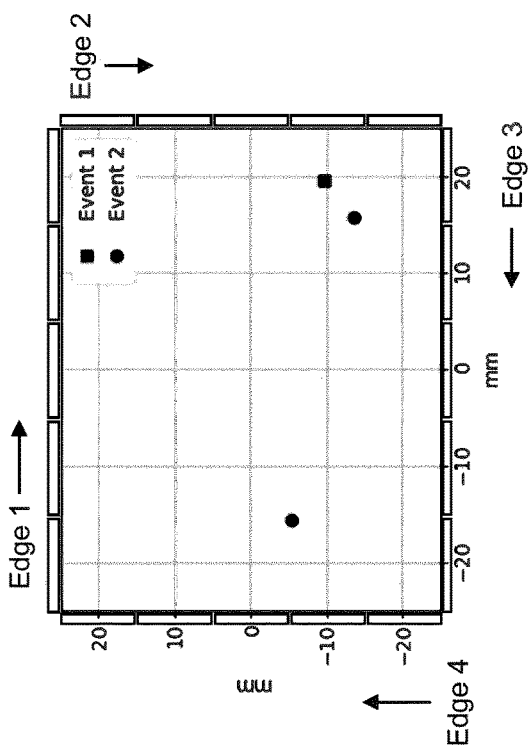
FIG. 20a
FIG. 20b

GAMMA RAY DETECTION SYSTEM AND CALIBRATION METHOD THEREOF

This application is the U.S. national phase of International Application No. PCT/EP2021/059665 filed Apr. 14, 2021, which designated the U.S. and claims priority to EP Patent Application No. 20170017.6 filed Apr. 17, 2020, the entire contents of each of which are hereby incorporated by reference.

TECHNICAL FIELD

The present invention relates to a gamma ray detection system for an ion beam emission apparatus, and a method of calibrating the gamma ray detection system. The ion beam emission apparatus may in particular relate to a medical apparatus, for ion beam therapy, for instance for proton beam irradiation of tumors. The detection system is for detecting gamma rays. The detection system may be used for dose and range monitoring during ion beam therapy treatment. The use of the detection system is not limited to irradiation therapy for human beings or animals: it can also be used as a conventional Positron Emission Tomography (PET) scanner or Compton camera for other uses.

BACKGROUND

Proton or ion beam therapy is one of the most precise methods of external radiation therapy. Unlike a photon beam, which has a high entrance dose and decreases gradually while passing through the body, an ion beam can penetrate through tissues and deposits most of its energy near the end of its track, known as the Bragg peak. In the present text, reference to the term "ion" in a general sense should also be understood to encompass negatively charged or positively charged ions, including protons.

In conventional ion beam systems for radiation therapy, the dose of irradiation is typically delivered by a narrow beam of a defined energy that is directed toward the targeted tissue zone, the penetration depth of the beam being controlled by modulating the energy of the beam. While passing through tissue, ions undergo nuclear reactions, some of which result in the emission of gamma rays. There are two types of gamma rays that can be detected for treatment monitoring: 1) Coincident gamma rays from the production of positron emission isotopes. 2) Prompt gamma rays from excitations of the target nuclei. The first type may be detected using positron emission tomography (PET) scanning to give information on exactly where in the patient an irradiation dose has been deposited.

Conventional PET-scanning used in the clinical processes may be performed:
- Off-line, whereby the PET-scan is made after irradiation, often with a delay of several minutes while the patient is transported from the irradiation room to another room housing the PET-scanner. Only isotopes with lifetimes in the order of minutes can be detected.
- In-room, whereby the PET-scan takes place shortly after irradiation, using a PET scanner located in the treatment room. Although the delay between irradiation and scanning is reduced compared to off-line systems, there is still some delay from moving the patient from the treatment position to the PET-scanner.
- In-beam, whereby measurement of positron annihilation activity occurs during irradiation by means of a customized PET scanner integrated into the treatment site or directly into the gantry. The real-time data acquisition allows for more accurate dose and range control, since gamma rays from short-lived isotopes may be detected.

Another per se known technique to verify the proton beam range is via the measurement of prompt gamma ray (PG) emission for instance using a Compton camera. PG emission is substantially simultaneous with proton beam emission and there is therefore essentially no delay between the emission and detection during treatment. PG detection thus allows rapid detection of significant range deviations; however, PG detection must be performed during treatment and image reconstruction is more complex to process.

Accurate detection of coincident gamma rays and prompt gamma rays may require calibration of the detection system.

In conventional segmented detectors, where an array of individual crystals is coupled to an array of photon detectors, it is sufficient to identify in which individual crystal a scintillating event occurred. One can thus determine the spatial coordinates of the scintillating event to a precision corresponding to the dimensions of the scintillating crystal. If a one-to-one coupling is used, where the light produced in one scintillator is coupled to a single photon detector channel, spatial calibration is superfluous.

Monolithic crystal gamma-ray detectors ("monolithic detectors") are increasingly used in PET-scanners. The most common configuration is a face-coupled detector, wherein a two-dimensional array of photon detectors covers one or two of the largest faces of a monolithic scintillating crystal. Such a configuration has a relatively short optical path length between the scintillating event and the photon detector but requires a relatively large number of photon detectors to cover the entire face. An alternative configuration is an edge-coupled detector, for instance as described in WO 2018/081404 A1, wherein light is collected at the edges of the monolithic scintillator. This reduces the total number of photon detectors but increases the optical path length. In either case, the advantage of monolithic detectors is that the spatial resolution is not limited by the finite size of an individual crystal segment, as it is in conventional segmented-crystal gamma-ray detectors. Another advantage of a monolithic detector is the potentially lower manufacturing costs, since the number of scintillating crystals and photon detectors can be reduced significantly.

For each scintillating event in a monolithic detector, several photon detectors will be exposed to light, and further analysis is required to determine the original coordinates of the scintillating event. The spatial calibration procedure, i.e. mapping the responses of multiple photon detectors to a position inside the monolithic scintillator is more complex than for a segmented detector. Known calibration methods include the following:

1: Calibration Using a Collimated Point Source

A first method of calibrating a monolithic detector is to expose it to a collimated source of radiation with known energy. As the position and direction of the incoming light is well known, each channel's response to the radiation can be characterized as a function of the coordinates of the absorbed radiation. The source may be moved relative to the detector by a robotic system in order to acquire sufficient data at different positions across the detector face. Such a process is time consuming and requires special equipment (the collimated source and robotic system) as well as complex control processes.

2: Multiple Fan Beams [Xin2019]

A second method is to expose the detector to multiple fan radiation beams, e.g. one fan in the xz-plane, another in the yz-plane and, possibly, a third in the xy-plane. A data processing algorithm is used to extract the common data set of the acquired signals from e.g. the two fans in the xz-plane and the yz-plane. This common data set corresponds to the intersection point of the two planes. Displacing the fan beams across the scintillator volume yields a full 3-dimensional spatial calibration of the detector. Although the number of calibration positions per fan beam can be greatly reduced compared to the number of calibration positions using a collimated source, this process similarly requires special equipment (fan sources, mechanical actuators) as well as complex control processes. This second method may be practical during manufacturing, however it has the following drawbacks for calibration of a detection system already installed at the end-user's premises (such as a hospital or a laboratory):

Installation of all auxiliary equipment required for the calibration is required.

Precise knowledge of the spatial distribution of scintillating events inside the scintillator is required, in order to properly select intersecting data subsets. Whereas this distribution is fairly straightforward to calculate using e.g. Monte Carlo simulations when a bare scintillator is directly exposed to the radiation source, for an already assembled detection system the geometry is vastly more complex;

Available space for positioning and aiming the fan beams may be limited;

Each scintillator must be individually calibrated;

Manual work is required to install the calibration equipment, perform the calibration and de-install the calibration equipment;

Use of possibly highly radioactive calibration sources will prohibit or limit access to the detector room during calibration.

3: Non-Collimated Source [Palomares2019]

A third method is to expose the detector to a non-collimated source of radiation, e.g. a point source, and acquire a large number of samples "blindly". This data set may then be further processed using a self-organizing technique, such as Kohonen's self-organizing map (SOM) [Kohonen1982]. If the number of individual photon detectors per scintillating crystal is M, the self-organizing technique essentially serves to map each sample of the M-dimensional data set to a 2 or 3-dimensional grid of neurons, or nodes, corresponding to the scintillator cross section or volume. Data samples that are similar in the M-dimensional space will become neighboring samples in the scintillator cross section or volume. Further corrections of the resulting sample density distribution in the scintillator volume may be required in order to match the predicted scintillation event distribution.

The advantages of this method include not requiring movable calibration equipment and the ability to calibrate multiple detector modules simultaneously.

However, some disadvantages are:

A detailed prediction of the scintillating event distribution inside each scintillator is required to properly correct the self-organized map. Monte Carlo simulations of each type of detector configuration is required.

For larger detector assemblies, a single source may be insufficient to yield a sufficiently large calibration set for all modules within an acceptable time owing to the distance between the scintillators and the source.

For larger detector assemblies, multiple sources or repeated movements of a single point source may still be required to calibrate all individual scintillators.

The path between the source and one or multiple scintillator detector(s) to be calibrated may be obstructed by an object (e.g. a table, couch or robotic arm), requiring successive calibrations where the obstructing object and/or the radiation source is moved The source must be accurately and precisely positioned with respect to each scintillator to be calibrated. As with the previous calibration methods, this could be difficult in an already assembled and installed system.

Manual intervention, transport and handling of possibly highly radioactive sources, and room occupation is still required to perform a calibration.

SUMMARY OF THE INVENTION

A general object of the invention is to provide a cost-effective and accurate gamma ray detection system for integration in an ion beam emission apparatus.

The ion beam emission apparatus in one of the specific applications is in the medical field for ion beam emission therapy.

A more specific object of the invention is to provide a gamma ray detection system that may be calibrated in an economical and efficient manner.

It is advantageous to provide a gamma ray detection system that may be calibrated in an automated manner without manual intervention, or with minimal manual intervention.

It is advantageous to provide a gamma ray detection system for portable or movable applications or for operational environments that may frequently change, that may be economically and efficiently calibrated for accurate and reliable detection.

It is advantageous to provide a gamma ray detection system that may be easily calibrated as required due to daily or seasonal changes in e.g. ambient temperature that may significantly affect the response of the photon detectors and require a new calibration.

It is advantageous to provide a gamma ray detection system for PET-scanning applications that may be conveniently and specifically calibrated to the primary gamma ray energy of interest (511 keV) with a high precision.

It is advantageous to provide a gamma ray detection system that may be conveniently calibrated and validated for all energies between 88 and 681 keV.

It is advantageous to provide a gamma ray detection system where relative timing offsets between individual photon detectors may be calibrated.

It is advantageous to provide a gamma ray detection system where energy-dependent timing offsets of individual photon detectors may be calibrated.

Disclosed herein, according to an aspect of the invention, is a gamma ray detection system comprising a computation system including a signal processing and control system, a detection module assembly including at least one detection module configured for detecting gamma ray emissions from a target zone, each detection module comprising at least one monolithic scintillator plate having a major surface oriented to generally face the target zone and lateral minor surfaces defining edges of the scintillator layer, and a plurality of photon detectors coupled to edges of said at least one scintillator plate and connected to the signal processing and control system. The monolithic scintillator plate comprises a material having isotopes intrinsically emitting radiation causing intrinsic scintillation events having an intensity measurable by the photon detectors. The gamma ray detection system comprises a calibration module configured to execute a spatial calibration procedure based on measurements of a plurality of said intrinsic scintillation events output by the plurality of photon detectors, the spatial calibration procedure for determining spatial positions of scintillating events in the scintillator plate as a function of the outputs of the photon detectors.

In an embodiment, said scintillator plate may comprise a scintillating material layer and radioactive material layer arranged on or adjacent to a major surface of the scintillating material layer, said radioactive material layer constituting said material having isotopes intrinsically emitting radiation.

In another embodiment, said scintillator plate may comprise a scintillating material synthetically doped with a radioactive material constituting said material having isotopes intrinsically emitting radiation.

In yet another embodiment, said scintillator plate may comprise a scintillating crystal containing naturally occurring isotopes, for instance Lutetium, and the calibration process uses intrinsic radioactive activity, for instance Lu-176 activity.

In an advantageous embodiment, the signal processing and control system comprises an energy filter configured to exclude photon detector measurement outputs above a pre-defined upper energy level.

In embodiments, the pre-defined upper energy level may have a value in a range from about 200 keV to about 1200 keV.

In advantageous embodiments, the pre-defined upper energy level may have a value in a range from about 200 keV to about 400 keV, preferably in a range from about 200 keV to about 230 keV, for instance around about 202 keV.

In embodiments the energy filter may further be configured to exclude photon detector measurement outputs below a pre-defined lower energy threshold.

In embodiments, the pre-defined lower energy threshold may be in a range from about 0 keV to about 90 keV.

In advantageous embodiments, the pre-defined lower energy level may have a value in a range from about 20 keV to about 90 keV, preferably in a range from about 65 keV to 90 keV, for instance about 88 keV.

In an advantageous embodiment, the gamma ray detection system comprises at least two scintillator plates, in particular stacked scintillator plates, and/or adjacently disposed scintillator plates, wherein the calibration procedure comprises measuring intrinsic scintillation events that are coincident between said at least two scintillator plates in order to select localized scintillation events from gamma rays with pre-defined energies of interest (e.g. 202 or 307 keV) emitted from one plate and absorbed in the other plate, and suppress the impact of a β-spectrum with unknown energy.

In an advantageous embodiment, the calibration module comprises an algorithm for computing a self-organizing map of a two-dimensional spatial position of intrinsic scintillation events in a scintillation plate.

In an advantageous embodiment, the gamma ray detection system comprises at least three scintillator plates, wherein the calibration procedure comprises measuring intrinsic scintillation events that are coincident between said at least three scintillator plates in order to select up to three localized scintillation events, one of them including contribution from a beta-electron.

In an advantageous embodiment, the calibration module comprises an algorithm for computing local variance-minimization to improve spatial resolution of the two-dimensional spatial position of intrinsic scintillation events near edges of the scintillator plate.

In an advantageous embodiment, a plurality of photon detectors are mounted against said edges configured to detect scintillation events in the scintillator plates from gamma rays incident on the major surfaces.

In an advantageous embodiment, the detection module assembly surrounds a target zone and includes a gap or orifice for ion beam emission therethrough.

Also disclosed herein is an ion beam therapy system for ion beam irradiation of a zone of tissue, comprising a patient support, an ion beam emitter movable relative to the patient support about at least an axis of rotation, and the gamma ray detection system.

Also disclosed herein is a method of calibrating a gamma ray detection system comprising a computation system including a signal processing and control system, a detection module assembly including at least one detection module configured for detecting gamma ray emissions from a target zone, each detection module comprising at least one monolithic scintillator plate having a major surface oriented to generally face the target zone and lateral minor surfaces defining edges of the scintillator layer, and a plurality of photon detectors coupled to edges of said at least one scintillator plate and connected to the signal processing and control system, the scintillator plate comprising a material having isotopes intrinsically emitting radiation causing intrinsic scintillation events having an intensity measurable by the photon detectors. The method comprises detecting an intensity and time of a plurality of said intrinsic scintillation events by the plurality of photon detectors, transmitting values of said detected intensities and times of scintillation events output by the plurality of photon detectors to a computing system, executing a calibration module program in the computing system to determine spatial positions of scintillating events in the scintillator plate as a function of the outputs of the photon detectors.

In an advantageous embodiment of the method, a self-organizing map of a two-dimensional spatial position of intrinsic scintillation events in a scintillation plate is computed by an algorithm of the calibration module.

In an advantageous embodiment of the method, a three-dimensional self-organizing map corresponding to two spatial coordinates and scintillating event energy is computed by an algorithm of the calibration module.

In an advantageous embodiment of the method, a local variance-minimization to improve spatial resolution of the two-dimensional spatial position of intrinsic scintillation events near edges of the scintillator plate is computed by an algorithm of the calibration module.

In an embodiment of the method, the calibration procedure comprises measuring intrinsic scintillation events that are coincident between said at least two scintillator plates in order to select gamma rays with pre-defined energies of interest (e.g. 202 or 307 keV) emitted from one plate and absorbed in the other plate, and suppress the impact of a β-spectrum with unknown energy.

In an advantageous embodiment of the method, photon detector measurement outputs above a pre-defined upper energy level are excluded.

In an advantageous embodiment of the method, photon detector measurement outputs below a pre-defined lower energy level are excluded.

In embodiments, the pre-defined upper energy level may have a value in a range from about 200 keV to about 1200 keV.

In advantageous embodiments, the pre-defined upper energy level may have a value in a range from about 200 keV to about 400 keV, preferably in a range from about 200 keV to about 230 keV, for instance around about 202 keV.

In embodiments of the method, photon detector measurement outputs below a pre-defined lower energy threshold may further be excluded.

In embodiments, the pre-defined lower energy threshold may be in a range from about 0 keV to about 90 keV.

In advantageous embodiments, the pre-defined lower energy level may have a value in a range from about 20 keV to about 90 keV, preferably in a range from about 65 keV to 90 keV, for instance about 88 keV.

Further objects and advantageous features of the invention will be apparent from the claims and the following detailed description of embodiments of the invention in relation to the annexed drawings.

BRIEF DESCRIPTION OF THE FIGURES

FIG. 1b is a schematic illustration of a detection module assembly of a gamma ray detection system according to embodiments of the invention;

FIG. 2a is a schematic perspective illustration of a scintillation crystal with edge-coupled photon detectors of a detection module assembly according to an embodiment of the invention;

FIG. 2b is a schematic perspective illustration of another embodiment of a scintillation crystal with face-coupled photon detectors of detection module assembly according to an embodiment of the invention;

FIG. 3a is perspective schematic view of a detection module assembly of a gamma ray detection system according to an embodiment of the invention;

FIG. 3b is a view similar to FIG. 3a with some photon detector support boards removed to see an inner portion of the detection module;

FIG. 3c is a detailed schematic cross-sectional view of a portion of a scintillator plate of a detection module according to an embodiment of the invention;

FIG. 3d is a simplified schematic view of a scintillator plate of a detection module comprising an electro-optical shutter (EOS);

FIG. 4 illustrates a decay scheme of Lu-176, with associated gamma ray and β energies;

FIG. 5 illustrates a plot of an example of absorbed energy spectrum from Lu-176 in a scintillator, indicating a suitable energy window for self-calibration (>88 keV and <202 keV) according to an embodiment of the invention;

FIGS. 18a to 18f are plots illustrating computation results of a generic SOM example, where a 2D-grid of nodes are mapped (trained) to samples on a 2D-grid; the lines indicate each sample's best matching unit (BMU);

FIGS. 19a to 19b are plots illustrating the effect of incorporating a density-correction mechanism into the SOM algorithm: in 19a, no density correction is applied (i.e. the original SOM method [Kohonen1982]), resulting in a clustering of samples near the corners and edges; in 19b, a density-correcting function was used on the same data, resulting in a more homogeneous distribution of samples;

FIG. 20a illustrates the locations of single (Event 1) and double (Event 2) scintillation events in an edge-coupled 50×50 mm scintillator, with five photon detectors per edge.

FIG. 20b illustrates the corresponding photon detector signals for Event 1 and Event 2 along the four edges.

Figure 1A:
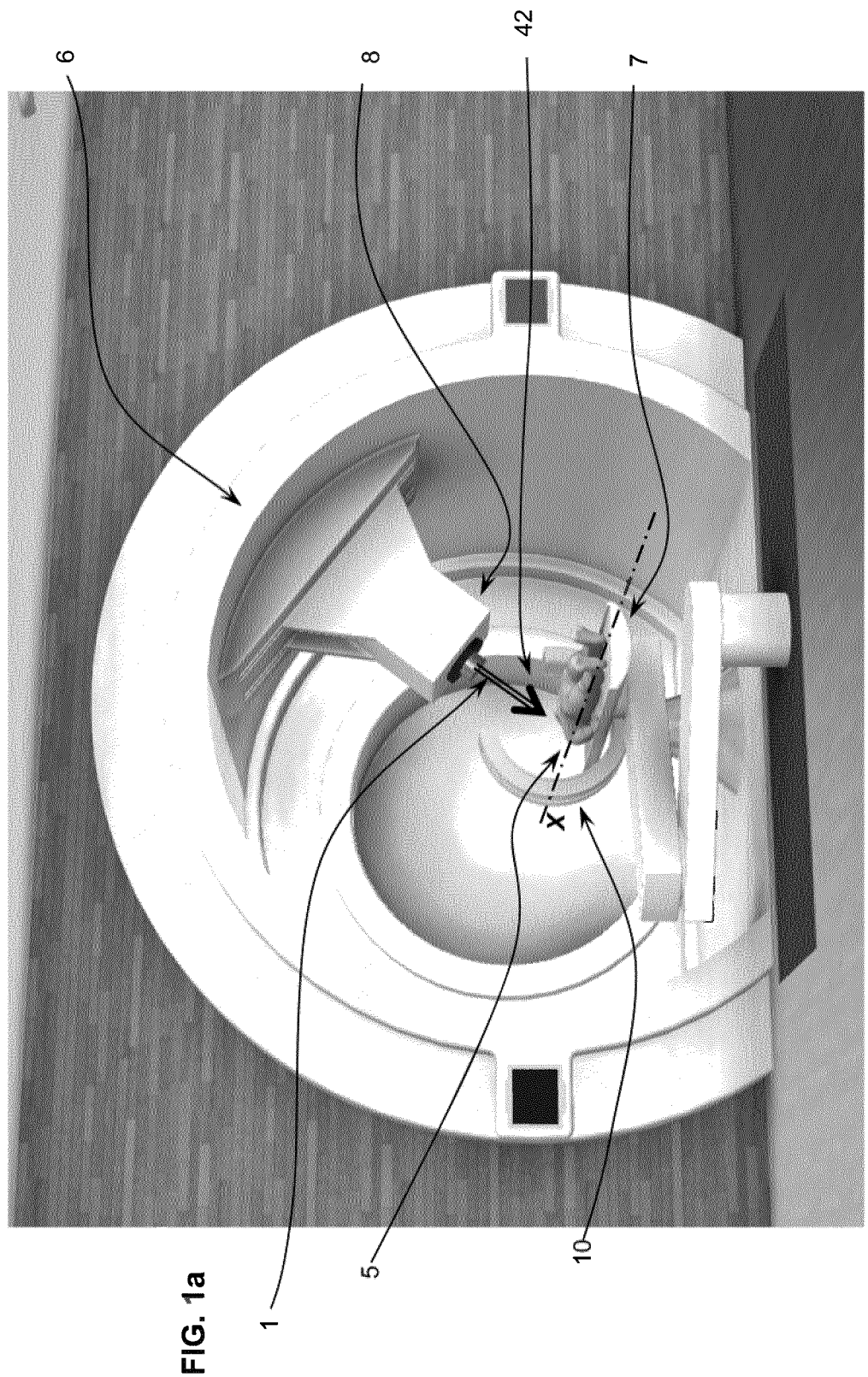
FIG. 1a is a perspective illustration of an ion beam therapy system with a gamma ray detection system, according to an embodiment of the invention.
Figure 6:
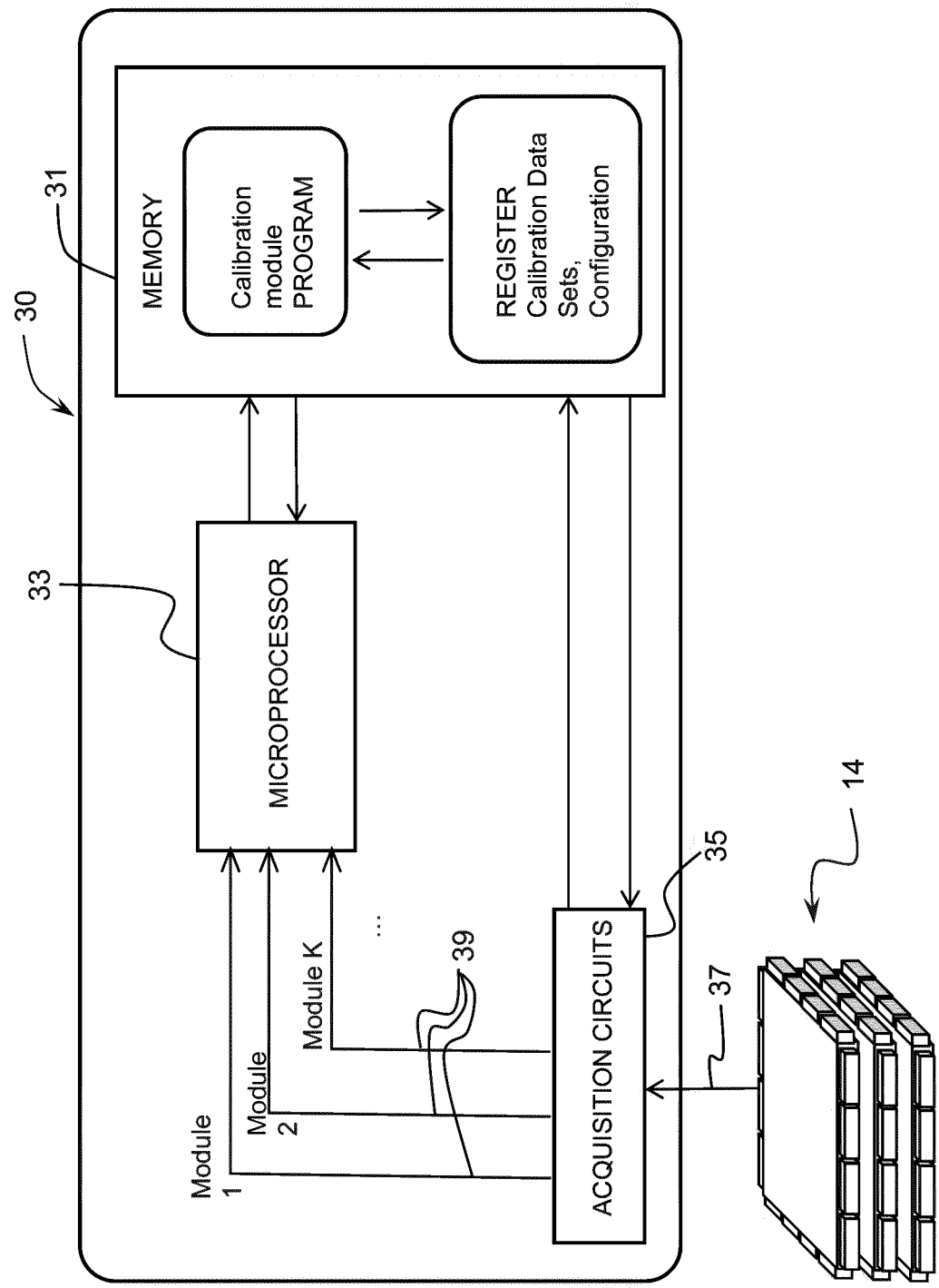
FIG. 6 is a block diagram of a computing system showing software modules and of a gamma ray detection system, according to an embodiment of the invention.
Figure 7:
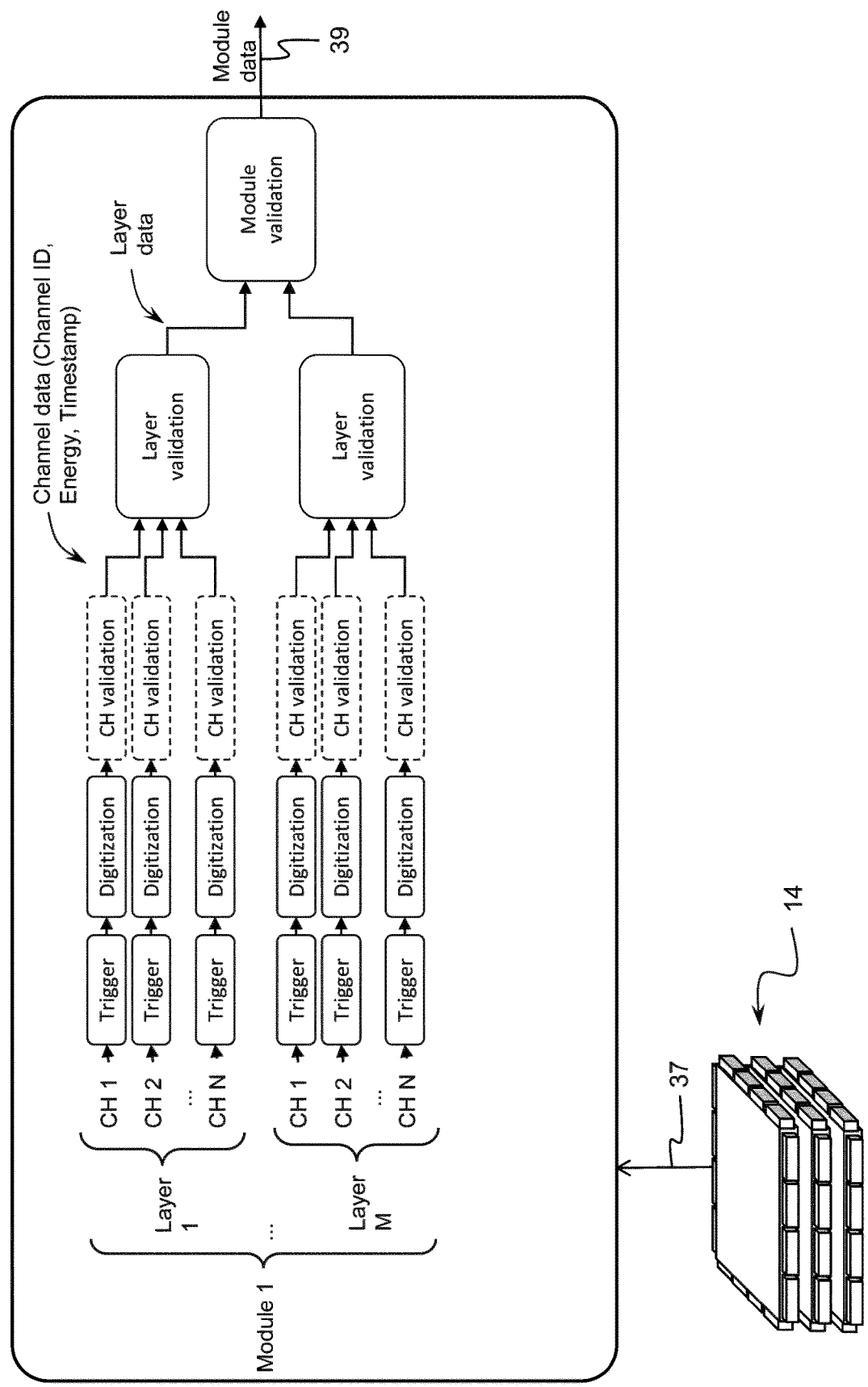
FIG. 7 is a block diagram of an acquisition circuit of the computing system of FIG. 6, connected to the outputs of the photon detectors, according to an embodiment of the invention.

Referring to the figures, starting with FIG. 1, an ion beam therapy system 6 in particular for ion beam radiotherapy, or for proton beam irradiation of a zone of tissue, according to an embodiment of the invention is illustrated. In this embodiment, a patient 5 is positioned on a patient support 7 that is mobile relative to an ion beam emitter 8 at least about an axis of rotation and a translation. The patient support 7 may in particular be movable at least in translation along at least one axis, in particular a horizontal axis X relative to a fixed reference (for instance ground), and the ion beam emitter may be rotatable around said horizontal axis X relative to a fixed reference (for instance ground). The patient support and/or the ion beam emitter may however be movable in translation and/or rotation along and around a plurality of axes, up to a fully three-dimensional movement allowing the ion beam emitter to be positioned at any position and angle relative to the patient.

The ion beam therapy system further comprises a gamma ray detection system 10. The gamma ray detection system 10 may, in certain embodiments, also be relatively movable with respect to the patient support along or around one or more axes. In an embodiment, the gamma ray detection system is movable along at least a direction of translation, in particular along the horizontal axis X, and in a variant also in rotation about said horizontal axis in coordination with the ion beam emitter 8.

In variants (not illustrated), it is possible to have a gamma ray detection system that is static with respect to a fixed reference, or that moves only in translation with respect to a fixed reference such as ground.

In a preferred embodiment, the gamma ray detection system 10 comprises a detection module assembly 13 that is generally ring or polygon shaped. In an embodiment, the detection module assembly may include an opening 42 to allow the ion beam emitter 8 to transmit ions (e.g. protons) through the opening such that the direction of emission of the ion beam emitter 8 is substantially in the same plane as the detection module assembly. This provides for a simultaneous and efficient detection of gamma rays emitted from the target zone receiving the ion beam. The detection module assembly 13 may for instance have a general "C" shape to provide an opening between opposed ends of the C shape to allow the ion beam emitter 8 to transmit ions through the opening. However, in variants, a substantially closed ring/polygon shape may be provided, for instance a generally cylindrical detection module assembly, with an orifice through a portion thereof to allow the ion beam 1 to be transmitted therethrough (variant not illustrated).

Depending on the imaging modality, images may be generated from processing of coincident detections of 511 keV positron-electron annihilation gamma rays and line-of-responses, LORs 27, or Compton camera image reconstruction from Compton cones 25. In some applications, it may be advantageous to utilize the intersection(s) 27b of LORs 27 and Compton cones 25 to generate the images.

The length of the detection module assembly 13 in the direction of the axis of rotation X of the ion beam emitter 8, may range from around 5-10 cm to around 50-100 cm, or 100-200 cm for a whole-body scanner, depending on the variant. For detection configurations with shorter axial lengths, a translation of the detection module assembly 13, possibly in conjunction with the ion beam emitter, may be effected during ion beam therapy. The detection module assembly may also be translated for scanning of the target zone, after ion beam emission, or during diagnosis (e.g. used as conventional PET scanner for example in the detection of cancer), according to an embodiment. With detection module assemblies having a length sufficient to extend over the entire target zone, it is possible to have a detection module assembly that is static with respect to the patient, whereby a displacement of the ion beam or ion beam emitter may not be followed by the detection system.

It may further be noted that the movement of the detection module assembly may be parallel or corresponding to the movement of the ion beam emitter or may follow a different movement configured to optimize the detection of prompt gamma rays and positron annihilation gamma rays emitted from the target as a function of the position of the target, the target environment, and the position and angle of inclination of the ion beam emitter 8. The optimal movements of the ion beam emitter and of the detection system may inter alia be obtained from calibration of the system on sample tissue.

An important advantage of the gamma ray detection system 10 used in the ion beam therapy system 6 according to embodiments of the invention, is that detection can be performed in real time during proton beam emission, capturing both prompt gamma rays as well as positron annihilation gamma rays. In addition, the positron annihilation gamma rays that are emitted during a certain time after proton beam emission, or between successive proton beam emission pulses during treatment, may be detected. This allows the proton beam absorption relative to the target zone to be continuously monitored, and, with feedback from the detection system, to be adjusted in order to have precise targeting of the target zone taking into account any movements of the target zone during treatment or after treatment and to avoid other problems such as wash out effects and the like that have been discussed previously in relation to conventional systems.

The prompt gamma rays emitted by the target may be detected with the detector functioning as a Compton camera whereas the positron annihilation gamma rays may be detected with the detection modules using a PET scanner functioning principle, both of these detection methods being integrated in the detection modules of the detection assembly according to embodiments of the invention. It may be noted that the PET detection may be operated during the ion beam emission, between ion beam emission and after ion beam emission, or alternatively may be switched on only between and after ion beam emission pulses. During ion beam emission, the rate of prompt gamma ray emission is very high which may render the measurement of coincident gamma rays from positron-emission annihilation less accurate and reliable, whereas for a certain duration after ion beam emission, prompt gamma ray emissions are low and positron annihilation gamma ray emissions continue for a certain time (as per se well-known) such that measurements can be performed during and after ion beam emissions.

The detection module assembly 13 comprises a plurality of detection modules 14. The detection modules 14 may, in an embodiment as illustrated in FIG. 2a, be arranged in an aligned manner to form segments. Various other configurations are however possible, whereby the number of modules aligned to form a segment or positioned in a substantially circular arrangement or in a polygonal arrangement (as illustrated) may be varied.

The detection modules 14 may be configured to function as both a Compton camera and a PET scanner.

Each detection module 14 may comprise one or a plurality of stacked scintillator plates 16 and a plurality of photon detectors 18 arranged to detect scintillation events in the scintillator plates.

According to embodiments of the invention, as schematically illustrated in FIGS. 2a, 2b and 3b, the scintillator plates have a major surface 40a oriented to generally face the target zone or axis Z, and lateral minor surfaces 40b defining the edges or contour of the scintillator plates. For simplicity, the lateral minor surfaces 40b shall also be named herein "edges".

In embodiments with a plurality of stacked scintillator plates, the stacking direction of the scintillator plates 16 in the detection module 14 is orthogonal to the major surface 40a.

According to a preferred embodiment, the photon detectors 18 are positioned on the edges 40b of the scintillator plates 16, for instance as illustrated in FIG. 2a. This is also referred to herein as an edge-coupled scintillator plate.

According to another embodiment, the photon detectors 18 are positioned on the major surface 40a of the scintillator plates 16 facing away from the target 4, for instance as illustrated in FIG. 2b. This is also referred to herein as a face-coupled scintillator plate. In embodiments with a plurality of stacked scintillator plates, the photon detectors may be positioned on the outermost scintillator plate furthest from the target 27c. A stack of face-coupled scintillators would typically have one array of photon detectors per scintillator layer in order to resolve separate events per layer; otherwise, one could just use a single, thick, scintillator. In variants, photon detectors may be positioned on each or on selected scintillator plates within the stack, the photon detectors being at least partially transparent to the coincident and prompt gamma radiation.

The detection module may comprise, according to embodiments, a stack of scintillator plates without a radial gap, or according to other embodiments, a stack of scintillator plates including a radial gap 17.

The radial gap 17 is in particular useful for the functioning of the Compton camera, whereby the innermost scintillator plates i.e. closest to the target zone act as scatter scintillator plates for the Compton camera, and the radially outermost stack of scintillator elements act as absorber scintillator plate or plates. The scatter scintillator plates may comprise one or more scintillator plates stacked closely together, and the absorber scintillator plates may comprise one or a plurality of closely stacked scintillator plates, depending on the variant.

The major surface 40a of the scintillator plates is the surface upon which the gamma rays are incident, and the edge 40b, which may be for instance substantially orthogonal to the major surface and extends between opposed sides of the scintillator plate, forms the edge of the scintillator plate along which the photon detectors 18 are arranged according to the preferred embodiment. In an edge-coupled detector context, the major surface 40a is either of the faces not optically coupled to photon detectors, whereby during calibration, gamma rays from neighboring layers may come from "above" or "below", and during detector operation, the majority of gamma rays comes from scanning object (target).

The preferred arrangement of photon detectors seeks to optimize the relationship between the accuracy of the depth of interaction (DOI) measurement (Z direction) and/or reduction in the number of readout channels, and the accuracy of scintillation position determination in the major surface of the scintillation plate (X-Y plane).

According to a preferred embodiment, along edges 40b of the scintillator plates, an edge light spreader material layer 26 may be provided. The function of the edge light spreader material 26 is to spread the scintillation light such that scintillation light from gamma rays incident on the scintillator very close to one edge 40b is spread sufficiently to be detectable by several photon detectors proximate said one edge.

According to a preferred embodiment, the edge 40b of the scintillator layer may further be provided with a detector-scintillator optical interface 22 comprising an interface material that optimizes optical transmission through the edge to the photon detectors and/or provides a consistent and predictable transmission of photons through the layer to avoid inconsistencies that may occur due to a non-constant interface (e.g. due to air, variable gaps and the like). The optical interface also serves to spread out the light from a scintillating event occurring close to the scintillator edge over multiple photon detectors in order to improve spatial resolution.

Along one or more of the scintillator layers, an electro-optical shutter (EOS) 24 may further be provided that is electronically operated to be switched on (optically transparent) or off (absorbing or reflecting), in order to allow photons to pass through the edge to the photon detector or to be blocked from passage to the photon detector, depending on the state of operation of the detector module 14.

It may be noted that the radial direction referred to herein corresponds to the direction Z indicated in the figures illustrating a detection module.

The photon detectors 18 arranged along the edges 40b of the scintillator plates 16 may be provided on a photon detector support board 20 that may for instance be in the form of a circuit board with circuit traces for connecting the photon detectors to a signal processing and control system 30 of the detection module 14.

The signal acquisition, processing and control system 30 of the detection module assembly 13 may comprise for instance circuit boards 32 and electronic components 34 mounted thereon, including for instance a microprocessor and a memory for processing and control of the detection modules. The circuit board 32 may be mounted at an outmost radial end of the module and comprise connectors 36a, 36b for connection of the circuit board 32 to the photon detector support boards 20 and further to an electronic control system of the gamma ray detection system 10 for image reconstruction.

The signal processing and control system 30 may form part of or be connected to a computing system that is installed in the detection module, or is external to the detection module, or may be in part external to the ion beam emission apparatus, it being understood that the execution of software and the computation and evaluation of data from the photon detectors may be performed in a centralized or distributed manner, within the electronic circuit of the detection module assemblies and/or in computing devices external to but connected to the hardware components of the gamma ray detection system.

In an embodiment for edge-coupled detectors, the support boards 20 may be configured as silicon photomultiplier array boards with edge connectors 36b that advantageously minimize the gap between adjacent detection modules 14 of the detection module assembly 13.

In another embodiment, for face-coupled photon detectors, the photon detectors may be mounted on one side of the circuit board 32 facing the scintillator plate. In a variant with face-coupled photon detectors on stacked scintillator plates, one or more support boards 20 may be provided to electrically connect to the photon detectors at each layer thereof.

In edge-coupled embodiments, the photon detectors 18 may comprise individual layer photon detectors 18a and/or strip multi-layer photon detectors 18b. In certain embodiments, the photon detectors 18 may comprise both strip multi-layer photon detectors 18b that extend radially (in the Z direction) across the edges of a plurality of stacked scintillator plates 16, and individual layer photon detectors 18a that are positioned on individual scintillator layers. A detection module 14 may comprise a plurality of strip multi-layer photon detectors 18b on each side of the module and in addition a column of individual layer photon detectors 18a on each side of the module or on only some of the sides, or on only one side depending on the variant. The individual layer photon detectors 18a enable the determination of the layer or layers in which the incident gamma ray is absorbed, whereas the multilayer strip photon detectors 18b (possibly in combination with the illuminated individual layer photon detector) enable the position of incidence of the absorbed gamma ray to be determined within the plane orthogonal to the radial direction (i.e. a plane parallel to the major surface 40a of the scintillator plate 16).

An important advantage of the use of strip multi-layer photon detectors 18b is to reduce the number of channels that need to be processed by the signal processing and control electronics for a given number of stacked scintillator plates, without reducing measurement accuracy. Thus, the data processing requirements are significantly reduced as well as the associated costs of the equipment, or alternatively greater accuracy in the depth of interaction measurement is obtained by having a larger number of stacked scintillator plates for a given number of readout channels.

When using monolithic scintillator plates as in the present invention, it is necessary to accurately determine at which position inside the scintillator crystal volume a scintillating event occurred, in order to ensure an accurate measurement. This requires a spatial calibration process since for each scintillating event, a large number of photon detectors (either edge-coupled or face-coupled) will be exposed to light, and further analysis is required to determine the original coordinates of the scintillating event.

According to an aspect of the invention, the calibration process is performed by executing a calibration software module in the signal processing and control system 30 and/or more generally in a computing system, using measurements by the photon detectors 18 of the intrinsic radiation of the material of the scintillator crystal 16. By exploiting the intrinsic radiation, the need for exposing the detector to an external source of radiation is eliminated, which is very advantageous for various reasons. Manufacturing costs of the apparatus as well as subsequent maintenance and operational costs are reduced since less equipment is needed. Moreover, as the intrinsic radiation is always present, calibration can be executed in the signal processing and control system at any time, without any need for manual intervention, setting up of motorized actuators or even entering the room where the detector is located.

The calibration process can be performed by a calibration software module executed in the signal processing and control system 30 receiving measurement outputs from the photon detectors without any manual intervention or control and thus can be fully automated and run at any time when the ion beam emission apparatus is not in operation. Furthermore, the intrinsic radiation is inherently stable, due to its long lifetime, and subsequent calibrations may be compared with previously computed calibration data stored in a memory of the signal processing and control system 30 throughout the operational lifetime of the detector, from manufacturing until disposal/dismantling.

Some of the most widely used scintillator materials used in conventional PET detectors contain lutetium: LSO (lutetium oxyorthosilicate), LYSO (lutetium yttrium oxyorthosilicate), and LSF (lutetium fine silicate). Natural lutetium contains 2.6% of the isotope Lu-176 which decays to Hf-176 with a half-life of $3.76 \times 10^{10}$ years. This results in an intrinsic background rate of about 307 Bq per $cm^3$ scintillator crystal. Lu-176 primarily decays via $\beta^-$ emission, followed by gamma emission as illustrated in FIG. 4. The kinetic energy of the emitted electron varies between 0 and 593 keV (99.66%) or 0 and 192 keV (0.34%).

According to an embodiment of the invention, the scintillator plate comprises a material that contains lutetium and the calibration process uses intrinsic Lu-176 activity.

The peaks in the energy spectrum [FIG. 5] correspond to absorption of one or more of the emitted gamma rays along the decay chain: 88 keV ($\gamma_1$), 202 keV ($\gamma_2$) and 307 keV ($\gamma_3$). The spectrum of the total energy deposited in the crystal depends significantly on the dimensions of the crystal, since this affects the probability of the gamma rays escaping the crystal or not and, to a lesser extent, the probability of the $\beta$-particle escaping. The energy spectrum is further complicated by the fact that the kinetic energy of the emitted/$\beta$-particle has a relatively wide distribution between 0 and 593 keV, the upper range being close to the sum of all the gamma rays.

For an ideal calibration source, the light should be emitted from a single (localized), known, point within the scintillator. However, the decay of Lu-176 in a scintillator crystal is neither occurring at an a priori known position, nor is the scintillation process occurring at a single point. Multiple gamma rays of different energies may be emitted. The mean distance required to absorb 50%, 95% and 99% of the emitted gamma rays are summarized in Table 1.

TABLE 1

Gamma ray and electron ranges in LYSO.

| $\gamma$ energy | $d_{0.5}$ | $d_{0.95}$ | $d_{0.99}$ |
| --- | --- | --- | --- |
| $\gamma_1$: 88 keV | 0.25 mm | 1.1 mm | 1.7 mm |
| $\gamma_2$: 202 keV | 1.8 mm | 7.7 mm | 11.9 mm |
| $\gamma_3$: 307 keV | 3.9 mm | 17 mm | 26.2 mm |

| $\beta^-$ energy | $R_{csda}$ |
| --- | --- |
| 100 keV | 28 µm |
| 200 keV | 86 µm |
| 593 keV | 0.4 mm |

The table also indicates ranges (continuous slowing down approximation rage, $R_{csda}$) of the emitted $\beta^-$-particles at different energies [Berger 2005].

In the case of 88 keV gamma emission, about 50% of the gamma radiation will be absorbed within about 0.25 mm of the emission point, and about 95% of the gamma radiation will be absorbed within about 1.1 mm. As also indicated in FIG. 4, the probability of gamma emission is only 15.5%: de-excitation via internal conversion is thus far more likely, resulting in an ejected orbital electron with an even shorter range. The binding energy for the 176-Hf K-shell is about 65.3 keV, so the kinetic energy of the ejected electron may be as low as 88-65.3=22 keV.

For 202 keV gamma rays, however, about 50% of the gamma radiation will deviate by more than about 1.8 mm from the emission point, before they are absorbed in the scintillator.

The invention is not limited to common inorganic crystal scintillators containing lutetium and is applicable to any scintillator that exhibits intrinsic radioactivity that produces practically characterizable scintillation events of a sufficient magnitude (number of scintillation photons), and rate (decays per second) for the described calibration procedure to be applicable.

A scintillator material that does not exhibit (sufficient) intrinsic radioactivity could be modified such that radioactive isotopes are introduced in the scintillating material, for example homogeneously throughout the scintillator volume, or homogeneously distributed in a coating (for example carbon coating, containing C-14 isotopes decaying via $\beta^-$-emission) or thin layer on or close to a scintillator surface 40a, during the scintillator or module manufacturing process. The choice of isotope would depend on the application.

One example is Sr-90, which decays via $\beta^-$-decay, with an electron energy up to 546 keV and a half-life of about 29 years. The lack of gamma emission, and the relatively short range of electrons (see Table 1 hereinabove), could be advantageous, since the scintillation light from a decay will be largely confined to the location of the decay. This reduces influence between different scintillators, and the event validation process could be simplified. Another advantage is that the emitted electrons are readily absorbed inside the detector, minimizing radiation exposure to patients and personnel.

Another example is Na-22, which decays via $\beta^+$-decay, followed by electron-positron annihilation, producing antiparallel 511 keV gamma rays. In a PET-scanner context, this would be advantageous for energy calibration of the detector since the gamma energy exactly matches the operational gamma energy of interest. However, during operation it could be problematic to distinguish between gamma rays emitted intrinsically and those from the target.

In low-Z scintillators, such as plastic scintillators, the stopping power of gamma rays is lower compared to common high-Z scintillators (LYSO, LSO, CsI(Tl), BGO, NaI (Tl)). To achieve a high spatial calibration precision, it would be advantageous to introduce a short-range $\beta^-$-source for intrinsic calibration.

Using $\gamma_1$ and Low Energy $\beta^-$ as Calibration Light Sources

If the scintillator volume is large compared to the ranges of the gamma rays, most gamma rays will be absorbed inside the scintillator, since most decays will occur within the bulk of the scintillator, and not close to the surface. However, if the scintillator is small compared to the ranges of the gamma rays, a significant fraction of the gamma rays will escape the scintillator without producing any scintillation light. These gamma rays may instead be absorbed in neighboring scintillators. Similarly, $\beta^-$-particles emitted close to the surface of the scintillator may also escape the scintillator.

The smallest energy corresponding to absorption of two gamma rays is 88 keV+202 keV=290 keV. In order to filter out scintillating events that may originate from two or more gamma rays, an upper energy limit of E<290 keV may be applied. But it should be noted that this energy could also be deposited by a single 88 keV gamma and a <202 keV $\beta^-$, or a 202 keV gamma and a <88 keV $\beta^-$. In the latter case, the $\beta^-$ would likely stop close to the emission point, whereas the 202 keV gamma could travel further before being absorbed: the scintillating light would essentially be emitted from two spatially separated locations, resembling two points sources. Compton scattering of any emitted gamma ray may also result in non-localized scintillation with a total energy below 290 keV.

In order to reject most non-localized events, the upper energy limit needs to be lower. With an upper energy limit of E<202 keV, mainly 88 keV $\gamma$-rays plus scintillation light from the $\beta^-$ will contribute to the measured light signal. The $\beta^-$-energy is in this case limited to 114 keV, or a range of a few tens of µm, which is well below the range of the 88 keV $\gamma$-ray.

In principle, a somewhat higher energy limit could be applied, if the energy limit is set such that the contribution from the $\beta^-$-particle is negligible compared to the contribution from the 202 keV $\gamma$. The scintillation light would then mainly come from a bright point source (the 202 keV gamma) and be polluted by a faint source from the $\beta^-$-particle.

However, in advantageous embodiments of the invention, the calibration method is applicable to an assembly of a plurality of monolithic scintillation detectors, possibly neighboring and close to each other. Since 202 keV $\gamma$-rays are more likely to be emitted in one scintillator and absorbed in another, it is advantageous in the aforesaid embodiments, to set the upper energy limit of acceptable events for calibration safely below 202 keV. This minimizes the impact of "pollution" between neighboring modules, and potentially different calibration precisions between modules at the center of the assembly, and peripheral modules of the assembly. As described later, some prior knowledge on the spatial distribution of scintillating events within the scintillator volume is necessary for a correct calibration. The simplest assumption is a homogeneous distribution of scintillating events within the scintillator. This is a fairly accurate assumption, if:

The electron ranges are short, compared to the scintillator dimensions. This is the case, even for primary $\beta^-$-energies close to the maximum 593 keV, for scintillator crystals with dimensions in the order of millimeters.

Only 88 keV $\gamma$-rays are taken into account (i.e. negligible contribution from neighboring modules)

Compton scattered gamma rays may occur, but for 88 keV gammas (and up to a few 100 keV), photoelectric absorption is dominant.

To conclude, the upper energy limit of scintillating events to include in the calibration data set is preferably below 202 keV, in order to exclude higher energy $\gamma$-rays.

The lower energy limit may, for example, be set to 88 keV. In practice, it mainly depends on the limitations of the acquisition and digitization instruments. If the lower energy limit is too low, the calibration data set may be polluted by events dominated by noise.

The upper energy threshold ultimately depends on the desired calibration precision. For e.g. a larger scintillator system with a coarse resolution, one may accept events where all gamma rays from a single 176-Lu decay were absorbed in the scintillator. The upper energy limit would then be 88+202+307+593 keV=1190 keV.

For an improved resolution, one may want to exclude events where $\gamma_3$ was absorbed. The upper energy limit may then be set to 307 keV or 307+88 keV=395 keV, if one makes the assumption that the $\gamma_1$ rarely escapes the scintillator.

For a better resolution, the $\gamma_2$ should also be excluded, as described above, with an energy threshold at around 202 keV.

If the photon detection system is very sensitive, and a very high precision is desired, one may wish to exclude the contribution from all gamma rays. In this case, the energy threshold should be set at low as 88-65.3 keV=22.7 keV, excluding even 176-Hf $\gamma_1$ de-excitations via internal conversion (IC) from the K-shell. Excluding $\gamma_2$ IC sets the energy threshold at 202-63.5 keV=138.5 keV, if one wants to exclude the possibility of $\gamma_1$-escape. Neglecting $\gamma_1$-escape sets the energy threshold at 88+202-63.5 keV=226.5 keV Using $\gamma_2$ and $\gamma_3$ as Calibration Light Sources Setting the upper energy threshold to <202 keV, for example 100 or 150 or 175 keV, as described in the previous section, could result in several photon detectors along the scintillator edges not triggering, due to the low amount of light. Many samples would thus contain elements that are zero. The magnitude of this problem depends on such factors as the exact choice of upper and lower energy trigger threshold, triggering scheme, number of photon detectors per side, readout noise, the choice of scintillator material, optical coupling efficiency, photon detection efficiency and digitization thresholds.

Figure 9:
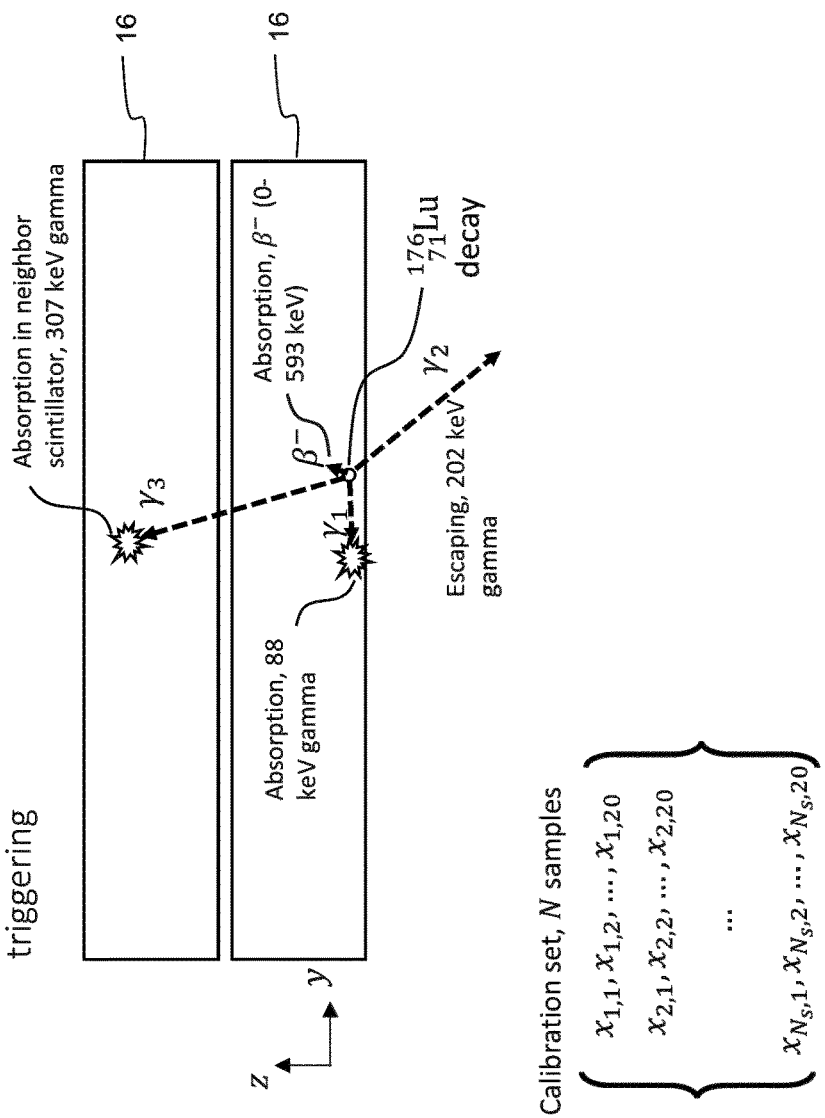
FIG. 9 is a schematic illustration of an example of two stacked scintillation plates showing a scintillating event occurring in one layer and the transmission of decay products therefrom.

In embodiments with multi-layer scintillator plates and edge-coupled photon detectors, one way of exploiting the higher energy gamma rays ($\gamma_2$=202 keV and/or $\gamma_3$=307 keV) would be to take advantage of the fact that these gamma rays may escape from one layer but be absorbed in a neighboring layer. These events could be identified by coincidence triggering between layers that are neighboring/close. If the energy deposited in one layer (roughly given by the sum of all photon detectors per layer) matches a suitable triggering window, corresponding to 202 or 307 keV, the sample from that layer could be used as a training sample for the self-organizing algorithm of the calibration software module described below. An example of such an event is shown in FIG. 9, where a 307 keV gamma escapes from a first layer, the decay layer, and is absorbed in a second layer.

Exploiting neighbor scintillator layers as sources of calibration radiation is advantageous from several aspects:
- The energy window of interest can be increased to a window region around 202 or 307 keV, which reduces potential problems of non-triggered photon detectors, or non-linearity issues when scaling up the self-organizing map weights (described below) from <202 keV up to e.g. 511 keV (the most common energy of interest in positron emission tomography), or even several MeV (for instance when using the gamma ray detector as a Compton camera, for instance for ion beam therapy range verification).
- 202 or 307 keV gamma rays yield sharp energy absorption peaks, unlike the signal from absorption of an 88 keV gamma ray plus the (unknown) energy of the emitted β-particle. The sharper peaks are more suitable to be used for energy calibrations, compared to the broad energy spectrum of $\gamma_1+\beta^-$.

Note that the term "neighbor" is not necessarily limited to major-face adjacent scintillators, since escaping gamma rays may pass through one or more scintillators before interacting.

Triple-Layer Events

In a dual-layer event, only one of the samples is used for calibration. In addition, only a fraction of dual-layer events are suitable for producing localized calibration samples, due to the high-energy threshold restriction imposed on one of the involved layers (FIG. 13b) in an attempt to identify absorption of 202 or 307 keV. However, there is still an ambiguity: the sample from the higher-energy layer may be incorrectly identified as the decay layer, since the high deposition energy could also be caused by simultaneous absorption or interaction with a 202 keV gamma ray and a 307 keV gamma ray escaping from the decay layer. The beta electron energy could also be such that the energy deposition in the decay layer is close to 202 or 307 keV absorption. In these events, the sample from the decay layer would be incorrectly used as calibration sample. Due to the energy spectrum of the beta electron (lower energies more likely), the energy of all selected calibration samples could be skewed toward lower energies.

It is also possible that calibration samples identified as e.g. absorption of a 307 keV gamma ray are, in fact, absorption of a 202 keV gamma ray plus a Compton scattered 307 keV gamma ray (or some other kinematic combination of gamma rays escaping from the decay layer, with a total energy deposition close to 202 or 307 keV). Such a misidentification would cause non-localized events to be used for spatial calibration, resulting in a distorted calibration map.

In an advantageous embodiment of the invention, triple-layer events are in addition or alternatively used to produce calibration samples. The 202 and 307 keV gamma rays may escape the first decay layer and interact in a second and third layer (possibly, but unlikely, also the short-range 88 keV gamma ray). If the escaped gamma rays are absorbed in the second and third layers, the energy deposition in the three involved layers allows identifying the underlying processes with a statistically high confidence: the second and third layer absorbing 202 and 307 keV, and the first layer an energy corresponding to 88 keV plus the beta electron energy. This type of event signature would be particularly advantageous for calibration since the energy deposition in all three layers is well localized. This type of event thus directly produces three well localized samples: one from the decay layer (localized, but energy not precisely known) and two of known energy (202 or 307 keV).

Specific Energy Calibration for 511 keV:

In order to calibrate and validate the detector for PET-scanning applications, it would be advantageous to expose it to a gamma ray source emitting 511 keV gamma rays. In an advantageous embodiment of the invention, the 202 and 307 keV gamma rays may be exploited for this. Identification of dual-layer events where the 202 and 307 keV gamma rays escape a first decay layer and are both absorbed in a second layer will produce an energy histogram peak at 509 keV, i.e. less than 0.4% difference from the primary energy of interest. In a conventional pixelated detector, the probability of simultaneous absorption of these two escaped gammas in the same scintillator pixel would be very low compared to the probability in the invention, which uses a layered, monolithic structure.

To summarize, three types of events induced by intrinsic radiation, and how to exploit them for calibration have been described:
- Single-layer events
  - A single layer triggered non-coincidentally with the other layers.
  - One (or multiple) energy windows are used to validate the event.
  - For spatial calibration, the energy window(s) should be defined such that they give confidence that the scintillating event was localized. In the case of LYSO, this necessitates rejecting $\gamma_2$ and $\gamma_3$, since they may travel far away from the decay point before being absorbed.

Figure 13B:
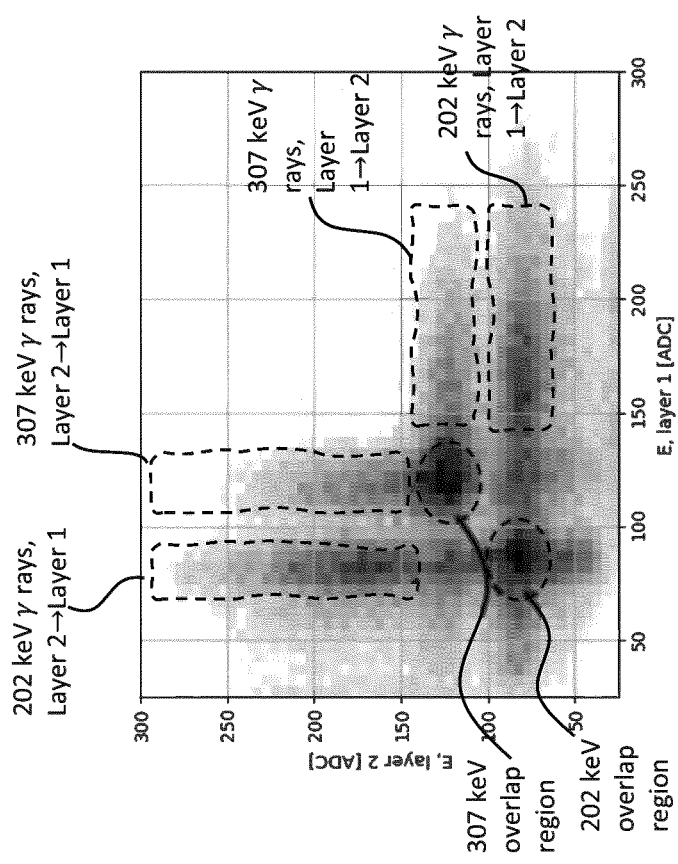
FIGS. 13a and 13b illustrate a 2D-histogram of the same events as in FIG. 12, whereby energies corresponding to $\gamma\_2=202$ keV and $\gamma\_3=307$ keV are indicated with dashed squares, FIGS. 13a and 13b showing different energy filter windows.

Dual-layer events
  Two layers triggered coincidentally
  Valid energy combinations for the two involved layers are defined, e.g. as in FIG. 13b, to identify that absorption of a single gamma ray of known energy occurred in one of the layers. In the case of LYSO, the energy in one layer should be about 202 or 307 keV (+/− some measurement precision margin).
  In addition, 202+307 keV events may be used to validate the detector's energy measurement accuracy near 511 keV.

Triple-layer events
  Three layers triggered coincidentally
  Energy windows are used to identify triple-layer events where the 202 and 307 keV gamma rays escaped from a first decay layer and were absorbed in different second and third layers.
  Each valid event results in three calibration samples from different three layers: two with known energy, and one with an unknown energy.

Sample Validation Process

A first validation step of potential calibration samples, based on energy windows and layer-coincidence, have been described above. Further validation steps may, for example, involve validation of edge profiles (such as concavity, convexity), comparison with previous calibration sets, the presence of non-triggered channels or involve the timestamp information from individual photon detector channels. Samples passing all validation steps are stored to a calibration set.

Figure 12:
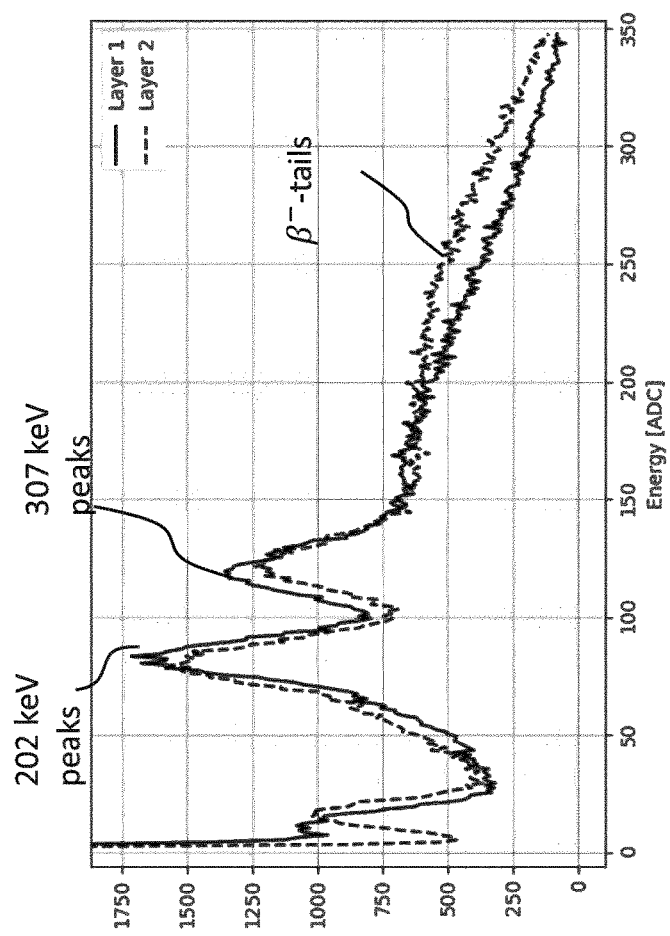
FIG. 12 illustrates a plot of experimental data from a monolithic 2-layer edge-coupled detector according to an embodiment of the invention, showing an energy spectrum of layer-coincidence events, where a nuclear decay occurred in one layer, and one or two escaping gamma rays were absorbed and detected in the other layer.
Figure 13A:
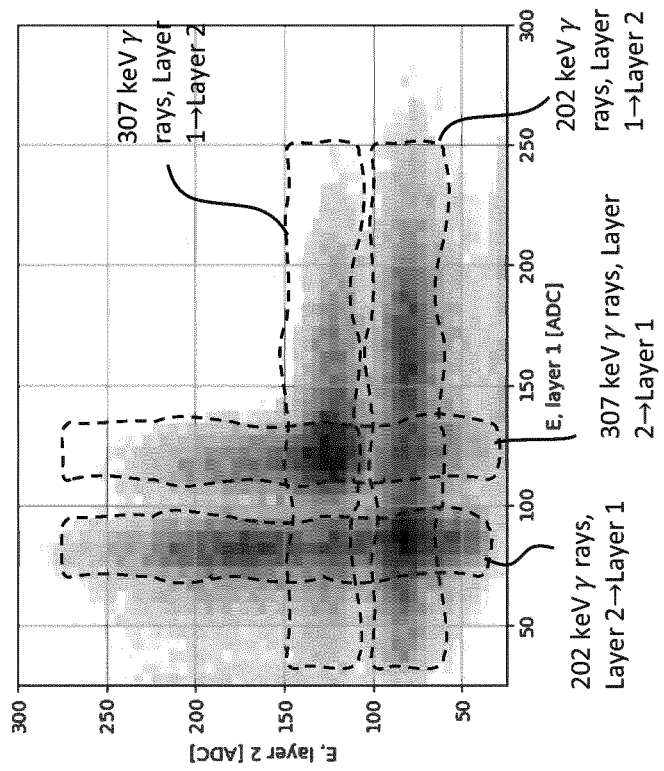
Figure 21:
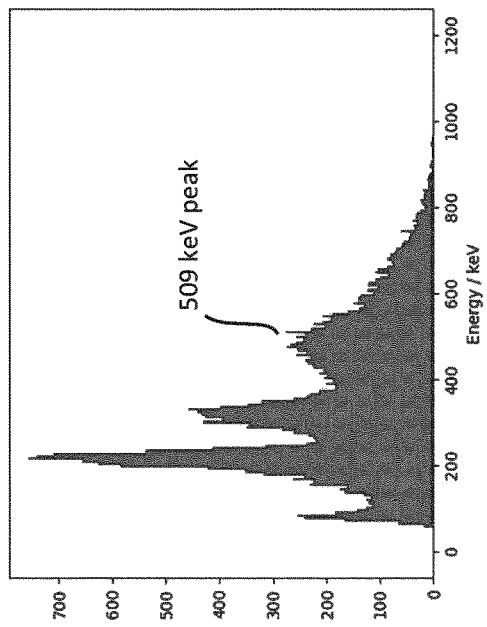
FIG. 21 illustrates an energy histogram of one detector according to an embodiment of the invention, using samples from dual-layer events, with the 202+307 keV energy peak indicated.

Experimental Validation of Invention
Experimental Setup
  Number of scintillator layers: 2 [FIG. 9]
  Dimensions of each scintillator layer: 26.5×26.5×3 mm
  Gap between scintillators: 13.8 mm
  Number of photon detectors per edge (layer): 8 (32)
  An example of 1-dimensional energy histograms for a 2-layer edge detector is shown in FIG. 12 for coincidence events. The energy is in ADC (Analog to Digital Converter) units and calculated as the sum of the ADC-value of all edge photon detectors per layer, and the peaks from 202 and 307 keV gammas are clearly distinguishable.
  A 2-dimensional histogram of the same data set is shown in FIGS. 13a, 13b. The 202 and 307 keV energy regions of each detector are visible as a vertically oriented region for Layer 1 and horizontally oriented region for the downstream Layer 2. The high-density overlap regions (dark areas) contain events where it is not clear in which layer the 202 or 307 keV gamma rays was actually absorbed, since the deposited energy in both layers matches 202 or 307 keV. Since the has an energy distribution between 0 and 593 keV, it is possible that one layer absorbed an 88 keV gamma ray plus the with an energy around 202−88=114 keV or 307−88=219 keV, while the other layer absorbed the 202 or 307 keV gamma ray. Other absorption schemes, involving e.g. Compton scattering, are also possible.
  The dashed rectangles indicate examples of coincidence trigger energy windows for events that may be used for the spatial calibration set. In principle, one could also include the overlap region mentioned above, since the range of the 88 keV gamma ray and the is relatively short, and the energy deposition can almost be considered point-like.
  Not visible in the energy spectrum are events where both the 202 and 307 keV gamma rays are emitted from one layer but absorbed in the other layer. For the scintillator detector configuration tested, the probability of this type of event was low. FIG. 21 shows an example from another setup where the 509 keV peak is more pronounced.

In order to execute an accurate spatial calibration by the calibration software module, it is advantageous to precisely know the spatial distribution in each scintillator layer of events involving absorption of 202 keV and 307 keV gamma rays from a neighboring scintillator layer. This can be readily computed or simulated in advance using e.g. Monte Carlo simulations under the assumption that the concentration of Lu-176 is homogeneous in the scintillator. For example, in a multi-layer configuration (>2 layers), central layers are more likely to absorb gamma rays from other layers, compared to the "top" and "bottom" layers, which lack neighbor layers on one side. In a multi-module configuration, inter-module escape (and scattering) of gamma rays may also need to be taken into account.

This calibration scheme may also be more susceptible to "edge effects" or "corner effects", compared to the single-layer scheme, i.e. the spatial and energy distribution of scintillating events may be significantly different closer to the surfaces of the scintillator than in the bulk. If instead 88 keV gamma rays and low energy $\beta^-$ are used for calibration, the event distribution inside the scintillator will be more homogeneous; since very few gammas and $\beta^-$ will escape the scintillator, the event distribution will be similar to the Lu-176 distribution, although deviations may be pronounced in the direct vicinity of the scintillator surfaces.

Coordinate Mapping

After acquisition of calibration data sets, post-processing by the signal processing and control system is necessary in order to link a particular sample to a 2D-coordinate across the scintillator surface. Two such methods are considered in embodiments of the invention: (1) Kohonen's self-organizing map (SOM), and (2) a local variance-minimization method devised by the inventors.

Calibration Training Set

Figure 8A:
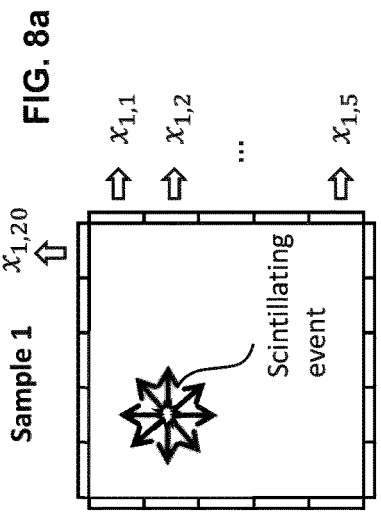
FIGS. 8a and 8b illustrate outputs of photon detectors coupled to a scintillator plate for a sampling process, showing the format of the calibration set: each sample is treated as a vector, and the response of each photon detector forms an element of the vector.
Figure 8B:
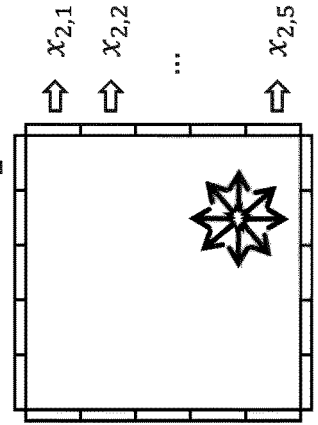

The calibration data set, forming a training set, consists of $N_s$ samples, each sample being a vector with dimension $N_k$. In the case of a square edge detector with $N_e$ photon detectors per edge, $N_k=4 \times N_e$, and the entire data set may be represented as a matrix with $N_s \times N_k$ (rows×columns). Examples are shown in FIGS. 8a, 8b, with $N_e=5$ photon detectors per edge.

Evaluation Set

Figure 10:
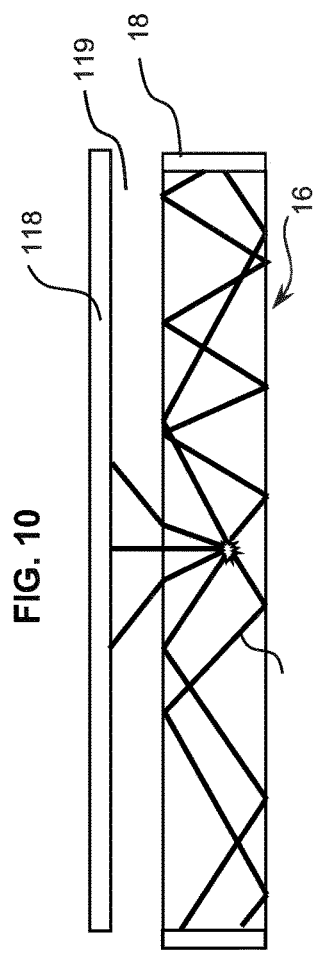
FIG. 10 is a schematic illustration of photon paths from a scintillating event inside a monolithic scintillator edge-coupled to photon detectors and surrounded by an air gap in the direction Z: most photons are totally internally reflected to the edges due to the large difference in refractive index between the scintillator and the air gap, whereas a small fraction of the scintillation photons directly escape the scintillator and reach a 2D-array of photon detectors at the other side of the air gap, which can be used to measure the original coordinates of the scintillating event.
Figure 11:
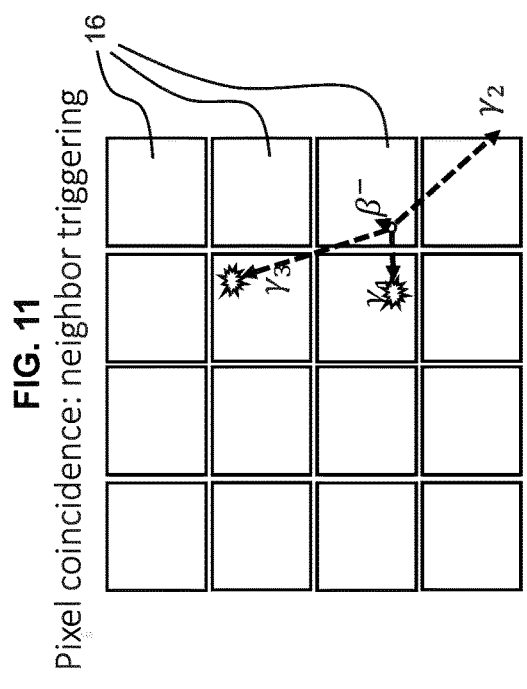
FIG. 11 is a schematic illustration of an example of energy calibration of a pixel detector using intrinsic radioactivity and pixel-coincidence events.

If the spatial coordinates of the calibration events are known, the calibration data set may further be split into more than one subset, e.g. a training set and an evaluation set. This is particularly useful for trimming and adjustment of the calibration parameters. In order to measure the position of intrinsic scintillation events, one could position a 2-dimensional array of photon detectors 118 close to either surface of the scintillator as illustrated in FIG. 10, with an air gap 119 above and below the scintillator 16. Due to the high refractive index of the scintillator, most of the photons (which are emitted isotropically) will reach the edge photon detector 18 via total internal reflection. However, a fraction of the scintillating photons will strike the 2D photon detector array 118, and this information can be used to determine the origin of the scintillating event. Knowing the origin may be advantageous for optimizing parameters and event validation criteria of the self-calibration procedure. In the case of multiple (>1) simultaneous scintillating events, this setup may also give information on the signature of these events, in order to be able to directly reject them for the calibration set, for example by training a machine learning algorithm with the signatures of single (localized, valid) and multiple (non-localized, invalid) scintillating events.

Kohonen's Self-Organizing Map

Principle: Computation of the SOM aims to map a 2-dimensional grid to a higher-dimension data set (here: the training set C) and does not require any prior knowledge on how individual samples are related to each other. Each node of the 2D-grid will be mapped to a higher-dimensional coordinate, resulting in a stretched, folded and distorted 2D-surface that aims to span the data points C as well as possible. Each data point is then linked to the closest grid point, or node. As described below, samples that are similar to each other will be linked to the same, or neighboring, nodes. In the context of self-calibration of a monolithic scintillator plate 16 according to embodiments of the invention, the SOM essentially divides the scintillator into a discrete grid. To initialize the SOM, the samples from the training set may then be randomly assigned to any point in the grid (other initialization strategies are possible). The iterative sorting algorithm of the calibration software module then aims to rearrange all samples such that:

Samples in the same grid point are similar, and:
Samples in neighboring grid points are also similar.

Since similarity between neighboring grid points is a criterion, the self-sorting algorithm will result in a globally ordered data set. Note that a fairly large number of samples (>>1 sample per grid point) are required to perform a reliable calibration.

Samples from scintillating events originating near the scintillator boundary (corners, edges) have more sample-neighbors on one side than the other. This asymmetry will cause the boundary samples to, eventually, diffuse toward the edges and corners during the sorting procedure.

The original SOM does not take into account the sample density, i.e. the number of samples per grid point, and it is a per se well-known artefact of this method that it tends to produce an artificially high sample density close to the boundaries (scintillator edges and corners). In the following, the inventors also propose a method to correct for this already during the iterative computation process, rather than as a post-optimization correction. The SOM can also be used to map the samples to a >2-dimensional grid.

Nodes

The $N_k$-dimensional data set is to be mapped to a 2D-grid, corresponding to the spatial extent of the scintillator in x and y. This grid is the set of nodes, which may, for example, be arranged in a Cartesian grid or a hexagonal grid or a staggered grid or another suitable grid style. For example, a grid with finer resolution near the edges may be employed. For simplicity, only a 2D Cartesian grid is discussed in the illustrated embodiments, but it will be apparent to one skilled in the art that the method can be applied to other types of grids. If the scintillator is not rectangular but for example a polygon with 3 or 6 sides, or bounded by at least one curved surface, the layout of the grid may be adjusted accordingly.

Weights

Each node i,j is associated with a weight vector $\overline{w}[i,j]$ of dimension $N_k$, that maps the node to a coordinate in the sample space. The principle of Kohonen's self-organizing map is that each data sample is mapped to the node with the weight vector most resembling the data sample (see "Best matching unit" below). In addition, the node weights are iteratively updated according to the neighboring node weights (see "Weight Adjustment" below).

Best Matching Unit (BMU)

One way of defining the "Best Matching Unit", or BMU, of a sample s is to find the node which weight vector has the shortest Euclidian to the sample, i.e:

$$BMU[s] = \min_{i,j}\left(\sum_k (s[k] - w[i,j,k])^2\right)$$

To one skilled in the art, it will be apparent that alternative BMU definitions are applicable, such as using the sum of |s[k]−w[i,j,k]|, or a filtering of low-weighted photon detectors, i.e. discarding k for which s[k] is below some threshold value.

Sample Normalization

Since the different samples may result from scintillating events of different energies and due to the stochastic nature of photon emission and photon detection, the number of detected photons will vary from sample to sample. The term "detected photons" is here used to indicate a scalar value from a photon detector. The actually measured quantity may be e.g. a (digitized) charge integral, a baseline-corrected charge integral, a time-over-threshold value, the number of fired single-photon avalanche diodes, or a similar quantity. Various sources of noise, instrumental artefacts and other imperfections will likewise cause sample-to-sample variations. In order to match samples of different energies to the Best Matching Unit of the weight vectors, it is necessary to perform some sort of normalization of the samples. For brevity, the inventors here describe the process using a straightforward normalization such that the photon detector sum of each normalized sample is equal to 1:

$$s[k] = \frac{s_{raw}[k]}{\sum_{k'} s_{raw}[k']}$$

Sample normalization is not necessary if all samples in an SOM have approximately the same energy.

Sample Corrections

The samples may be subject to other corrections before normalization. Such corrections could, for instance, consist of subtracting the expected number of dark counts from each photon detector, or multiplying individual photon detectors or groups of photon detectors (for example, photon detectors along the same scintillator edge, or photon detectors coupled to the same scintillator layer) with some scaling factor to compensate for variations in quantum efficiency or optical coupling efficiency, based on analytical calculations, simulations or previous calibrations.

Neighbor Function

The neighbor function is a measure of how close two nodes $(i_1, j_1)$ and $(i_2, j_2)$ are, and a key factor in the optimization procedure. The traditional neighbor function is a Gaussian:

$$\beta[i_1, j_1, i_2, j_2] = e^{-\frac{\Delta^2}{2\sigma^2}}$$

Where, for a Cartesian grid:

$$\Delta^2 = (i_2-i_1)^2 + (j_2-j_1)^2$$

and σ is a parameter that, typically, initially is large enough that nodes at the opposite end of the node grid can attract each other (if similar), but then decreases in size with an increasing number of iterations, and the node weights converge toward some final value. For nodes that are separated by more than some upper distance threshold W, the neighbor function may be truncated to zero, for example W=2σ or W=3σ.

To one skilled in the art, it will likewise be apparent that neighbor functions of different characteristic shapes may be used, for example:

$$\beta = \cos^2\left(\frac{\pi\Delta}{2W}\right)$$

$$\beta = \left|1 - \left(\frac{\Delta}{W}\right)^m\right|^n \left(\text{e.g.}\left(1 - \left(\frac{\Delta}{W}\right)^3\right)^3 \text{ or } \left(1 - \left(\frac{\Delta}{W}\right)^2\right)^2\right)$$

(for nodes separated by more than W, the neighbor function takes the value 0).

Often, an exponentially diminishing value is used for σ:

$$\sigma_t = \sigma_0 e^{-\frac{t}{\tau_\sigma}}$$

where t is the iteration number.

Weight Adjustment

Weights are updated according to:

$$w_{t+1}[i,j,k] = w_t[i,j,k] + \alpha_t \beta_t (s_{norm}[k] - w_t[i,j,k])$$

α is a parameter defining the attraction between a node and a sample, and typically lies in the range [0,1], e.g:

$$\alpha_t = \alpha_0 e^{-\frac{t}{\tau_\alpha}}$$

To one skilled in the art, it will be appreciated that other schemes for gradually reducing the value of σ and α may be used.

Density and Corrections

At the end of the iterative self-organization process, the spatial sample density is given by the number of BMU-matched samples per node. This density should ideally match the expected distribution of scintillating events in the scintillator region. However, with a standard BMU-matching, as defined above, sample clusters of higher density tend to form at the scintillator corners, along the edges and close to the center of photon detectors. This is a density artefact that do not reflect the real distribution of scintillating events, and it will distort the mapping from sample to scintillation event coordinates. Two examples of methods to correct for this artefact are:

1. Post-optimization corrections, as suggested in Palomares2019 (Using Monge-Kantorovich optimization: Delzanno 2008)
2. Forcing the sample density to better reflect the expected scintillating event distribution already in the optimization process.

In an advantageous embodiment, the inventors propose to implement the density forcing by adjusting the BMU-matching to:

$$BMU_{corr}[m] = \min_{i,j}\left(f(\rho[i,j]) \times \sum_k (s[k] - w[i,j,k])^2\right)$$

Here, the function $f(\rho[i,j])$ is a function of the sample density $\rho[i,j]$ which serves to reduce the attraction of already highly populated nodes, resulting in a more homogeneous density. One implementation of $f(\rho)$ is to simply set $f(\rho)=\rho$, or even $f(\rho)=\rho^p$ ($p \geq 1$, for example p=2, p=3 or p=4) in order to make highly populated nodes more "repelling".

An example of a comparison between the final self-organized map, with and without density correction, is shown in FIGS. 19a and 19b, with each sample plotted around its respective BMU-node (node grid=24×24). The edge-clustering effect is clearly visible in FIG. 19a, whereas the sample density is more homogeneous in FIG. 19b.

The density function may be adjusted according to the expected scintillating event distribution, $\rho_{ref}[i,j]$, as given by e.g. Monte Carlo simulations, such that under-populated nodes (compared to the Monte Carlo-reference) have a higher attraction, and over-populated nodes have a lower attraction. The density correction could then be a function of, for example, the ratio $\rho[i,j]/\rho_{ref}[i,j]$.

Speed-Up: Adaptive Grid Density

The computational time required for the self-optimization can be significantly shortened by using a successively refined simulation grid:

1. Initialize the node grid and node weights on a coarse grid, e.g. $N_i^0 \times N_j^0$.
2. Run the optimization for a fixed number of iterations, or until some convergence criteria is met
    a. The convergence criteria could be that the change in node weight vectors is below some threshold value
3. Increase the grid density to $N_i^1 \times N_j^1$
    a. σ and W may be scaled to smoothly match the new grid resolution
4. Interpolate new node weights on the finer grid
5. Repeat from point 2. until the desired spatial resolution is met.

Speed-Up: Reduced Sample Set

Another method to shorten the computational time is to successively increase the number of samples participating in the self-organizing process. One could start with a relatively low number of samples (per node), and gradually, or stepwise, include more and more samples in the optimization procedure, as the node weight maps are gradually converging. For example, each time the grid density is increased, one could introduce more samples participating in the self-organizing process, such that the mean number of samples per node is constant.

Sample Elimination

Samples that appear to be significantly different from neighboring samples may be eliminated. Such samples may be caused by electronic noise. Another possible cause is coincidental scintillating events, for example photo-electric absorption of one 88 keV gamma ray in one point, coincidentally with a Compton scattered 202 keV gamma ray at another point. The total energy could be within the acceptance window, but since the light originates from two different locations, the photon detection pattern of such an event would be distorted compared to scintillation light from photoelectric absorption of a single gamma ray.

FIG. 20a shows an example of an event originating from a single point (Event 1), and another event originating from two different locations (Event 2). FIG. 20b illustrates the corresponding response of the photon detectors along each edge. Whereas Event 1-like events normally yield convex or monotonically increasing/decreasing edge-profiles, Event 2-like events may yield concave edge-profiles along one or more edges, depending on the distance between the scintillating events and the relative energies of the individual scintillating events. The characteristic shape of the edge profiles may therefore be used to validate a sample.

Criteria for acceptable edge-profiles may be used to discard samples that are likely to originate from multiple, coincident but spatially separated scintillation events.

Such criteria may be based on:
Analytical calculations
Simulations
Measurements using e.g. a radioactive calibration source or an electron beam
Measurements using a light source, to mimic scintillation light
Data from previous calibrations
Identification of calibration samples that strongly deviate from neighboring samples (for example Euclidian distance).

Data and validation criteria based on the first five categories may be used for rapid identification of samples to discard. In the context of calibration based on a self-sorting algorithm, the last category requires performing at least a preliminary spatial sorting of the data in order to identify sample neighbors and deviating samples. A machine learning algorithm could be used for identification of Event 2-like events.

According to an embodiment of the invention, a set of initial calibration data is pre-defined and stored in a non-volatile memory 31 of the signal processing and control system 30, the pre-defined calibration data corresponding to acceptance criteria for events that are close to point-like, i.e. where most of the scintillation light production occurs within a volume segment that is sufficiently small compared to the desired spatial resolution. This facilitates the process of mapping the acquired calibration data set to a 2-dimensional map corresponding to the transverse spatial dimensions of the scintillator, since individual samples are "clean", in the sense that the light source is resembling a point source.

Weight Map Orientation

Since the organization process is unsupervised, it is possible that the convergent weight maps are not correctly orientated with respect to the physical locations of the photon detectors on the scintillator. The weight maps may, for example, be mirrored along the x- or y-axis, or rotated 90, 180 or 270 degrees along the z-axis. Since the physical locations of the photon detectors are known, this can easily be automatically corrected by flipping, mirroring or rotating the weight maps such that the position of the maximum value of each weight map coincides with the known position of its associated photon detector.

Weight and Variance Maps

When the optimization procedure has converged to a final solution, one can calculate maps of mean weight and variance at each node, for each photon detector k:

$$\mu[i,j,k] = \langle X_{ij}[k] \rangle$$

$$\sigma_\mu^2[i,j,k] = \langle (X_{ij}[k] - \mu[i,j,k])^2 \rangle$$

Where $X_{ij}$ is the subset of the data with a BMU in node (i,j).

The mean and variance may be calculated only from non-zero sample elements, or only from sample elements passing some other qualification metric (for example: outlier rejection).

Lowess Maps from BMUs

The quantities $\mu[i,j,k]$ and $\sigma_\mu^2[i,j,k]$ are calculated only from the samples whose BMU is the node [i,j]. The finer the grid, the fewer samples per node, and the more susceptible the mean and variances are to artefacts and noise. In order to maintain a fine spatial resolution (by using a fine node grid), while still suppressing noise due to a low number of samples per node, according to an embodiment of the invention, the system may take the additional step of further smoothing the BMU maps by applying a 2-dimensional locally weighted regression, Lowess smoothing, for example of order 1 on $\mu$ and $\sigma_\mu^2$ (higher orders could also be used).

Self-Organizing Kohonen Map—Example

The principle of the self-organizing procedure can be illustrated by mapping a 2-dimensional set of samples to a 2-dimensional grid of nodes. In the example illustrated hereafter, the samples consist of a 25×25 grid of points in the window $x \in [0,3]$ and $y \in [0,3]$, which are mapped to a 7×7 set of nodes. Density heterogeneities are punished proportionally to $\rho^4$.

FIG. 18a illustrates the mapping after 0 iterations. The samples are plotted as circular markers. The weight vectors of each node are of the same dimensions as the samples, and each node's weight vector is plotted as a square. The BMU, or best matching node, of each sample is drawn as a line between the sample and the matching node. Likewise, lines are drawn between neighboring nodes, i.e. between node (i,j) and (i−1,j), (i,j−1), etc. At 0 iterations, the nodes' weight vectors are randomly generated.

FIG. 18b illustrates the mapping after 4 iterations. The nodes are now distributed over a narrow region within the center of the samples. After 60 iterations (FIG. 18d), it is starting to become apparent that the nodes are "disentangling", becoming sorted. Note that each sample's BMU is not necessarily the closest node, as a consequence of the density correction: if the most similar BMU of a sample is already populated by many other samples, another node will likely be selected as BMU. After 140 iterations (FIG. 18e), the node weights have spread out over a large fraction of the region spanned by the samples. After about 490 iterations (FIG. 18f), the node weights have converged to a stable solution.

Local LOWESS Variance Minimization

In another embodiment of the invention, an alternative to Kohonen's self-organizing map is proposed to overcome a weak point of the Kohonen SOM, which suffers from artefacts close to the edges and corners of the nodes' boundary region (i.e. close to the scintillator edges and corners), limiting the spatial precision. At the center of the scintillator, each node, or neuron, is competing for samples with surrounding neurons on all sides. The nodes at the boundary, however, are only competing for samples with neurons that are closer to the center of the scintillator. This asymmetric competition will have the effect that the gradients of the node maps of mean photon detector responses, $\mu[i,j,k]$, are suppressed at the boundaries. To some extent, this could be overcome by refining the grid, but at the cost of a longer computational time, since the number of nodes increases quadratically with grid resolution, plus the fact that a larger calibration set is required to maintain the mean number of samples per node at a statistically acceptable level.

This advantageous method according to an embodiment of the invention aims to minimize the local variance at each node. This feature is taken as a natural property of the correctly organized calibration set. An example of the procedure may be as follows:
1. Define a node grid, corresponding to the spatial coordinates of the physical scintillator's (x, y)-extent.
2. Optionally, initialize all samples to the node coordinate corresponding to the sample barycenter (in the case of a monolithic face-coupled detector). In the case of a monolithic edge-coupled detector, one example of initialization coordinates is the average barycenter from photon detectors on opposite edges. Other initialization coordinates are possible, for example applying a linear scaling to the barycenter values to cover a larger fraction of the scintillator surface.

3. From the assigned coordinates of all samples, generate locally weighted 2-dimensional regression maps ("LOWESS maps") of all photon detectors k across the scintillator surface x, y: $\mathcal{L}_\mu(t=0,x,y,k)$ and $\mathcal{L}_\sigma(t=0,x,y,k)$.

4. Iterate over all samples $m \in [0, N_s]$ and move each sample to its best matching node on the Lowess maps. The inventors have tried different metrics of "best matching node", with similar results (t denotes epoch):
   a. Local-variance minimization:
      i.
      $$BMU_m(i, j, t+1) = \min_{i,j}\left\{\sum_k \left(s_m[k] - \mathcal{L}_\mu(t, x[i], y[j], k)\right)^2\right\}$$
   b. Maximum-likelihood minimization:
      i.
      $$BMU_m(i, j, t+1) = \min_{i,j}\left\{\sum_k \left(\frac{(s_m[k] - \mathcal{L}_\mu(t, x[i], y[j], k))^2}{\mathcal{L}_\sigma(t, x[i], y[j], k)^2}\right)\right\}$$
   c. From the new set of BMUs, calculate new Lowess maps for epoch t+1.
   d. Similarly to what the inventors proposed for the SOM, the BMU matching can be adjusted to directly take sample density into account. In the case where one wishes to achieve a homogeneous sample density, one could simply adjust a) above to, for example:
      i.
      $$BMU_m(i, j, t+1) =$$
      $$\min_{i,j}\left\{\max(0.5, \rho^4[i, j]) \times \sum_k \left(s_m[k] - \mathcal{L}_\mu(t, x[i], y[j], k)\right)^2\right\}$$

where $\rho[i,j]$ is the number of samples at node [i,j]. Overpopulated nodes are then more repelling than under-populated nodes. Here, an exemplary minimum density value of 0.5 was used to avoid the same numerical value (0) on all non-populated nodes ($\rho=0$). This is mainly of importance in the beginning of the calibration procedure, when some nodes have not yet been populated, or if the mean number of samples per node is low.

5. Repeat step #4 until the solution converges.

In order to reach a stable solution, according to an advantageous embodiment, a wide radius for the 2-dimensional Lowess regression at the beginning of the calculation is used (similarly to Kohonen's neighbor function using a successively shrinking value of a).

Likewise, it is also possible to successively increase the grid resolution, for example after a pre-defined number of epochs, or when some stability criterion is met (for example based on the amplitude of the change of Lowess maps elements from one epoch to the next). Considering the case of a monolithic edge-coupled detector with $N_e$ photon detectors per edge, or a monolithic face-coupled detector with $N_e \times N_e$ photon detectors, one could start the optimization with a grid of $N_e \times N_e$ nodes, and then increase the number of nodes per edge until the desired spatial resolution is met.

Different variations of Lowess regression are possible, e.g. using different types of weight functions. In addition, if the samples are assigned to discrete nodes, one could also make e.g. a linear, quadratic or bicubic interpolation from the mean and variance of the samples assigned to each node, or similar interpolation techniques from the sample set.

One may limit the number of samples moved to a new BMU in each iteration to a fraction of all samples, e.g. 25% or 50%, to stabilize the algorithm.

The primary advantage with this technique is that, since the Lowess maps are generated from a local interpolation, the map values at the edges are less constrained by the more central samples, which allows for steeper edge gradients.

Monte Carlo Validation: Kohonen's SOM Vs. Local-Variance Minimization

In order to compare the precision of Kohonen's SOM vs. the local-variance minimization method according to an advantageous aspect of the invention, the inventors used a data set of Monte Carlo simulations, where a fixed energy gamma beam was aimed towards a 50×50×6 mm scintillator in a 1×1 mm grid, from −24.5 mm to +24.5 mm (50×50 grid points). The advantage with using a Monte Carlo validation is that the coordinates of each scintillating event are precisely known.

The scintillator was equipped with 5 photon detectors along each edge ($N_k$=5×4=20). For each gamma ray-scintillator interaction, the scintillating photons were tracked until absorbed by a photon detector or another medium. The number of photons detected by each detector was logged. A large data set (>500,000 samples) was stored, along with the x, y-coordinates of each gamma ray. A fraction of this data set was used as training data for both a SOM, and a local-variance minimizer, using the same final number of nodes in both cases (30×30 nodes). Lastly, the predictive ability for the two optimizers was tested by using a set of validation samples (not used in the training): each sample in the validation set was matched to its BMU, and the difference between coordinates of the matched BMU and the actual interaction coordinate of the gamma ray (the input coordinate in the Monte Carlo simulation) was calculated.

Of particular interest is to compare the precision of the two techniques for samples close to the scintillator edges. Defining the center of the scintillator as x=y=0, one can evaluate the spatial error, $\Delta=\sqrt{\varepsilon_x^2+\varepsilon_y^2}$, the Euclidian distance between the real scintillating event coordinate and the coordinate of the matched node, as a function of r=max(|x|, |y|) (which is zero at the center, and +25 mm at the scintillator edges).

Figure 16:
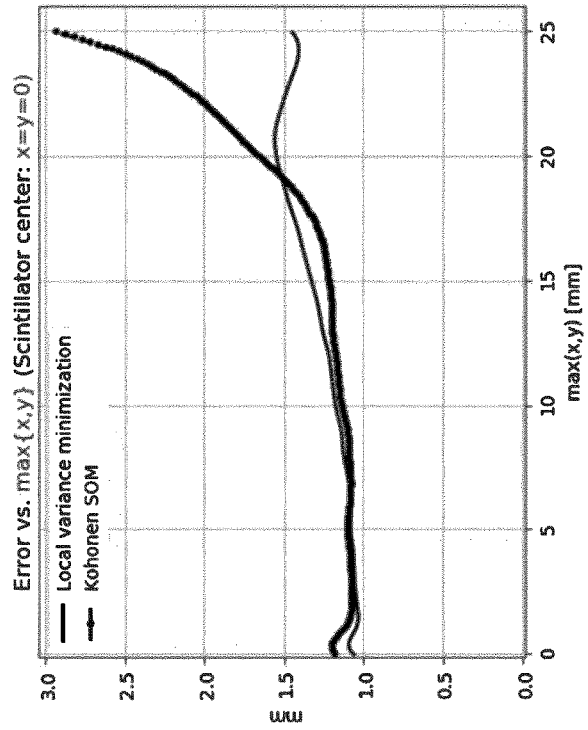
FIG. 16 illustrates a plot showing a comparison of spatial precision using Kohonen's self-organizing map and a local-variance minimization technique according to an embodiment of the invention, whereby the error is plotted as a function of maximum coordinate distance from the scintillator center.
Figure 17C:
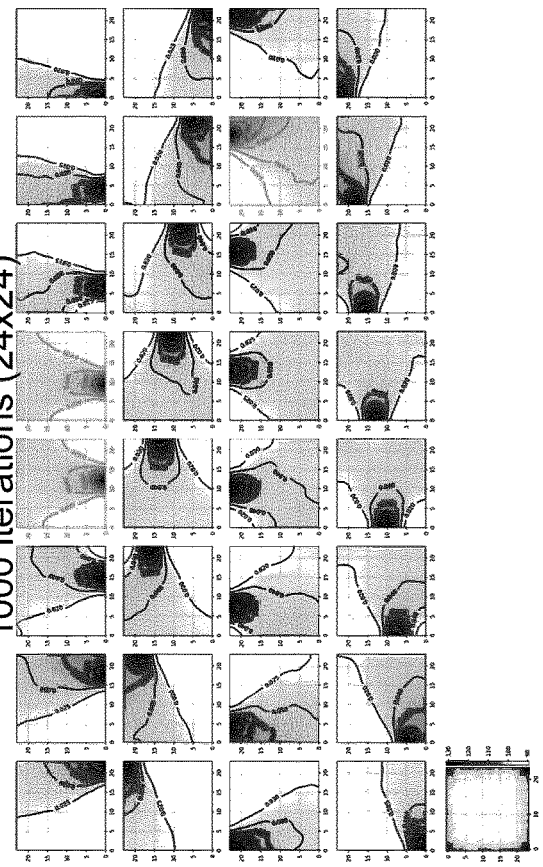
Figure 17B:
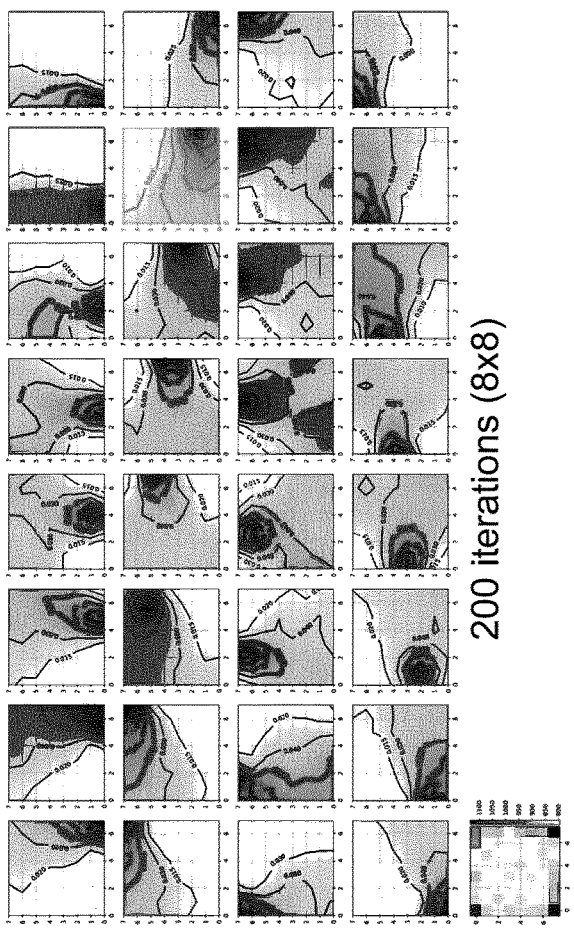

FIG. 16 illustrates $\Delta$ as a function of r for both SOM and the local-variance minimization technique (1-dimensional Lowess regression of $\Delta(r)$ for the entire evaluation set). In the central region of the scintillator (r<20), the two techniques give similar precision. However, at the outskirts of the scintillator (r≥20), the local-variance minimization produces a significantly better spatial precision: up to a factor two at the edges (r=25).

It is important to note that the outer 5 mm of the scintillator (r∈[20, 25]) represents 36% of the scintillator surface, or more than one third of detected events. The technique of local-variance minimization according to an advantageous embodiment therefore represents a significant improvement on the overall spatial precision—not only for spatial calibration using intrinsic radioactivity, but also for spatially calibrating any monolithic detector using an external source of radioactivity.

Laboratory Validation

This section describes an experimental validation setup, and results from data acquisition. It is to be understood that any numbers, such as dimensions, specifications, threshold values, number of pixels per edge, scintillator material, photon detector types, etc. are merely examples for illustrative purposes and other configurations and values are possible within the scope of the invention.

Figures 14, 15A, 15B:
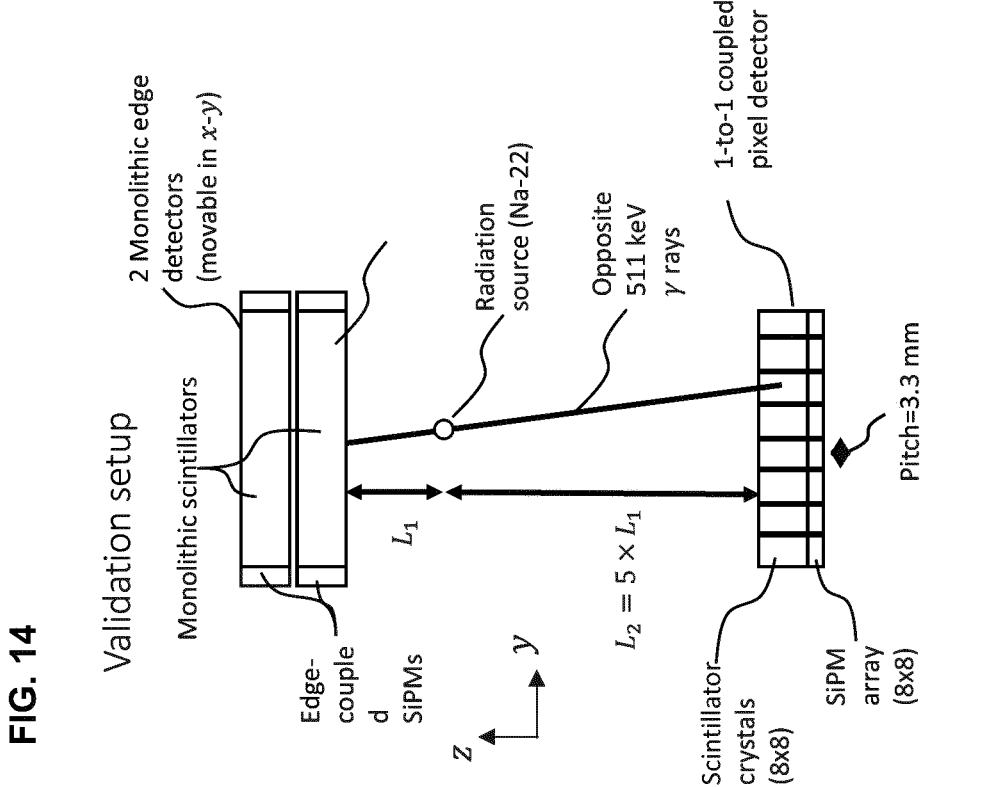
FIG. 14 illustrates schematically an experimental validation setup of an embodiment of the invention, showing an edge-coupled monolithic scintillator placed on one side of a radioactive source (Na-22), whereas a pixel detector is placed on the other side. Coincidence triggering of the monolithic and pixel detector is used to acquire data from opposite positron-annihilation 511 keV gamma rays. By placing the pixel detector further from the source than the monolithic detector, the spatial calibration resolution at the monolithic detector can be better than the pitch of the pixel detector.
FIGS. 15a and 15b illustrate a histogram of the spatial precision using a single-layer calibration set (all events <202 keV) (FIG. 15a) and a histogram of the spatial precision using a 2-layer calibration set (coincident events matching absorption of a single 202 keV gamma ray) (FIG. 15b)
Figure 17A:
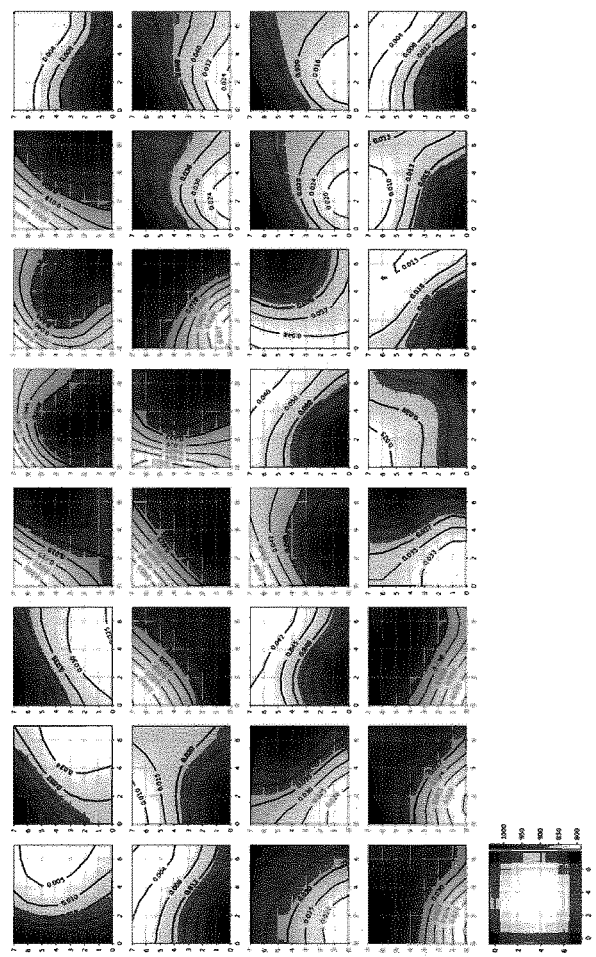
FIGS. 17a to 17c illustrate plots of the mean photon detector response maps computed from experimental laboratory data for a monolithic scintillator plate with edge-coupled detectors having eight photon detectors per edge, whereby the different plots show the maps at different iterations.

To test the feasibility of the invention, the inventors built a square edge-coupled monolithic detector, using 2 layers of LYSO scintillators with 8 photon detectors per scintillator edge. The monolithic detector was placed on one side of a radioactive point source (Na-22, 0.25 mm diameter), opposite an 8×8 scintillator array detector coupled to an 8×8 SiPM (silicon photomultiplier) array, 3.3 mm pitch. The monolithic detector was placed closer to the source than the pixel detector, as illustrated in FIG. 14. At positron annihilation, two opposing and coincident 511 keV gamma rays are emitted from the source. The position of the gamma ray being absorbed in the pixel detector is known, and the position of the gamma ray being absorbed in the monolithic detector can be inferred via a line-of-interaction from the pixel detector via the point source, to the monolithic detector. By placing the pixel detector further away from the source than the monolithic detector, the spatial resolution at the monolithic detector can be better than the pitch of the pixel detector.

The validation procedure steps were the following:
1. Acquiring photon detector data from intrinsic radioactivity on the monolithic detector
2. Generate two separate calibration sets:
   a. Calibration set 1, $C_1$: single-layer event. An energy filter corresponding to 88-180 keV was applied, rejecting all events outside the window
   b. Calibration set 2, $C_2$: 2-layer events, using 202 keV gamma rays. Only events where both scintillator layers triggered were used. Further filtering was implemented by only accepting events where the energy deposition in Layer 1 was 220 keV±20 keV, and the energy deposition in Layer 2>300 keV. This selects most events where a $\gamma_2$ emitted from Layer 2 was absorbed in Layer 1.
3. Generate calibration maps, according to Kohonen's SOM or a local variance minimization for the two calibration sets.
4. Insert a radioactive source and acquire data from coincident events on the monolithic detector and the pixel detector.
5. Using the calibration maps from Step 3 and monolithic samples from Step 4, predict which pixel was triggered on the pixel detector. Compare with the pixel which was actually triggered and calculate the spatial difference in x and y at the monolithic detector, $\varepsilon_x$ and $\varepsilon_y$.

Histograms of $\varepsilon_x$, $\varepsilon_y$ and the absolute error $\sqrt{\varepsilon_x^2 + \varepsilon_y^2}$ using calibration sets $C_1$ and $C_2$ are displayed in FIGS. 15a and 15b. For $C_1$, 50,000 samples were used for training, and for $C_2$ 20,000 samples. The median value of the absolute error is approximately 1 mm for both calibration sets.

Simultaneous Energy and Spatial Calibration Using Triple-Layer Events

The production of localized calibration samples using triple-layer described above would produce calibration samples of undefined energy in the decay layer (88 keV plus beta electron energy). The deposition energy of these samples would essentially be taken from a continuous energy distribution. As such, these samples are well suited for use in a 3-dimensional self-organizing map, which may be implemented in a similar fashion as described above: the transverse coordinates x and y being two parameters, and the deposition energy being the third parameter. By way of example, one may use a 3-dimensional calibration node grid, where one of the dimensions corresponds to energy deposition.

Figure 22:
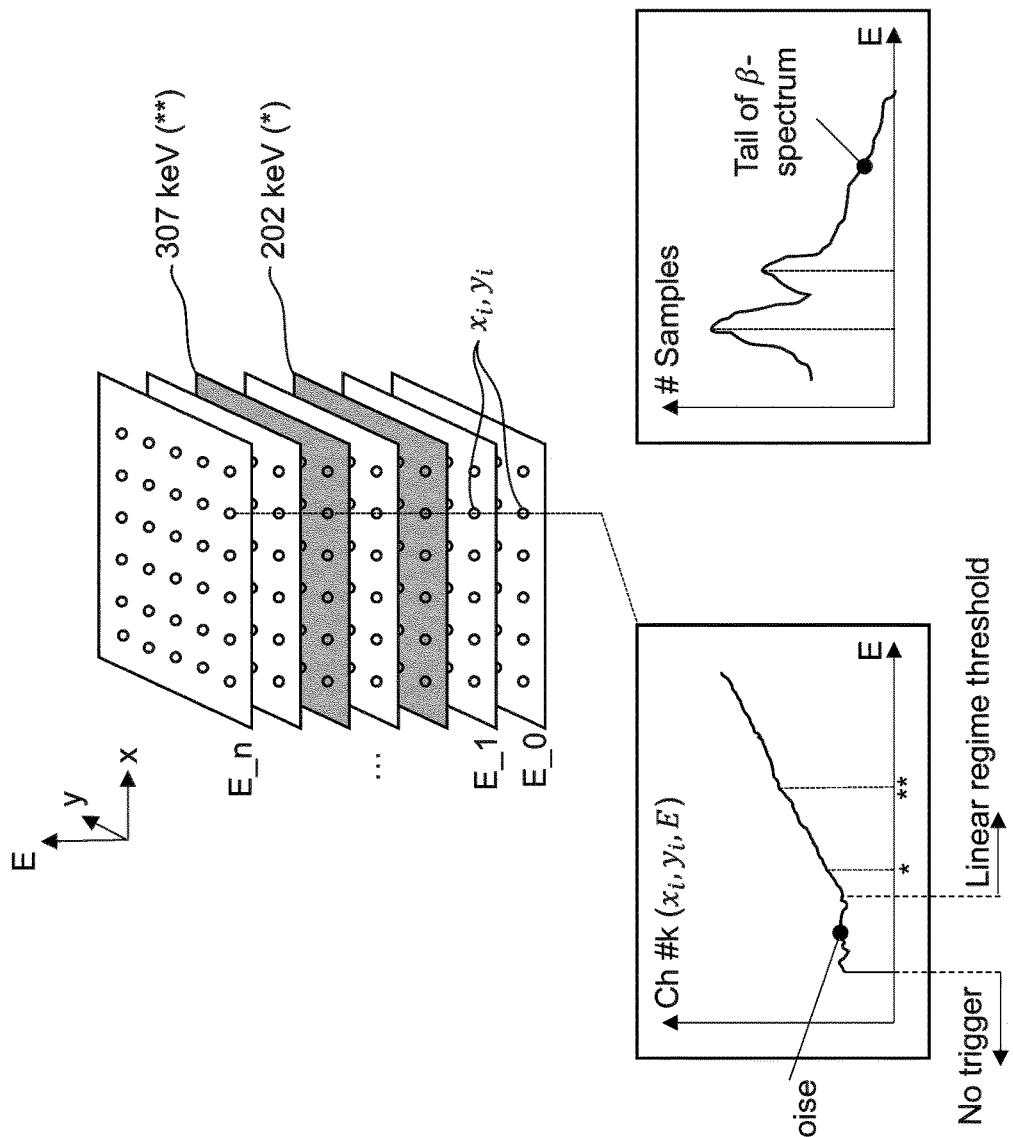
FIG. 22 illustrates graphically the principle of a 3D SOM, or simultaneous spatial calibration and energy characterization of a layer.

Alternatively, one may arrange the calibration samples in a set of multiple individual SOM-maps, each map corresponding to a minor energy range E_0, E_1, . . . , E_n, as illustrated in FIG. 22. Prior to sorting, samples may be assigned to a particular SOM according to, for example, the sample sum of all photon sensors, which correlates to scintillation energy. The previously described SOM algorithms may be adapted to cover the additional dimension by regularly updating the lowess maps with the interpolated lowess map along the energy dimension, which serves to maintain the individual lowess map in a monotonic energy order. Samples are free to move between different maps when applying the BMU matching.

Upon convergence, the final number of samples per lowess map (i.e. per minor energy range) will reflect the energy histogram, with a high energy tail corresponding to the beta electron spectrum, and peaks corresponding to 202 and 307 keV. This sample frequency per minor energy range may be used to calibrate the detector response for localized events of all energies between 88 and 681 keV. This method solves the specific problems related to sample-normalization when comparing samples of different energies.

Lookup Table

The calibration output may be stored electronically in the form of a lookup table for faster reconstruction of scintillation coordinates.

LIST OF FEATURES REFERENCED IN THE FIGURES

Patient 5
Target zone (e.g. tumor) 4
Ion beam therapy system 6 (e.g. Proton beam therapy system)

Patient support 7
Ion beam emitter 8
  Ion beam 1
Gamma ray detection system 10
  Detection module assembly 13
    Opening 42
    Detection module 14
      Scintillator plate / layer 16
        Major surface 40a
        Minor (lateral) surface 40b (also named "edge")
      Radial gap 17
      Photon detector 18
        Individual layer photon detector 18a (also named "photon detector pixel" or just "pixel")
        Strip Multilayer photon detector 18b (also named "photon detector strip" or just "strip detector")
        Photon detection output signal 37
      Photon detector support (board) 20
      Detector-scintillator optical interface 22
      Electro-optical shutter (EOS) 24
      Edge light spreader 26
Computing system
  Signal processing and control system 30
    Non-volatile memory 31
    Circuit board 32

-continued

Electronic components 34
   Microprocessor, Memory
   Connectors 36a, 36b
Coordinate mapping evaluation set-up
   Array of photon detectors 118
   Air gap 119
Compton cone 25
Line of response (LOR) 27
   Compton cone - LOR intersection 27b
Volume of interest (target zone) 27c

PRIOR ART REFERENCES

Patent Literature

U.S. Pat. No. 10,393,895 B2 (Palomares2019)
WO 2019/183594 A1 (Xin2019)

Non-Patent Literature

Alva-Sanchez2018: H. Alva-Sänchez et. al, *Understanding the intrinsic radioactivity energy spectrum from $^{176}Lu$ in LYSO/LSO scintillation crystals*, Scientific Report 8, Art 17310 (2018)

Afanaciev2015: Afanaciev, K. G., Artikov, A. M., Baranov, V. Y. et al. Response of LYSO:Ce scintillation crystals to low energy gamma-rays. Phys. Part. Nuclei Lett. 12, 319-324 (2015). https://doi.org/10.1134/S1547477115020028

Kohonen1982: Kohonen, T. Self-organized formation of topologically correct feature maps. Biol. Cybern. 43, 59-69 (1982). https://doi.org/10.1007/BF00337288

Berger2005: Berger, M. J., Coursey, J. S., Zucker, M. A., and Chang, J. (2005), *ESTAR, PSTAR, and ASTAR: Computer Programs for Calculating Stopping-Power and Range Tables for Electrons, Protons, and Helium Ions* (version 2.0.1). [Online] Available: http://physics.nist.gov/Star. National Institute of Standards and Technology, Gaithersburg, Md. [accessed 2020 Jan. 31].

Delzanno2008: G. L. Delzanno et. al, *An optimal robust equidistribution method for two-dimensional grid adaptation based on Monge-Kantorovich optimization*, Journal of Computational Physics 227 (2008) 9841-9864. https://doi.org/10.1016/j.jcp.2008.07.020

OTHER REFERENCES

Kohonen's Self-Organizing Map description:
https://en.wikipedia.org/wiki/Self-organizing_map

The invention claimed is:

1. A gamma ray detection system comprising a computation system including a signal processing and control system, a detection module assembly including at least one detection module configured for detecting gamma ray emissions from a target zone, each detection module comprising at least one monolithic scintillator plate having a major surface oriented to generally face the target zone and lateral minor surfaces defining edges of the scintillator layer, and a plurality of photon detectors coupled to edges of said at least one monolithic scintillator plate and connected to the signal processing and control system, the at least one monolithic scintillator plate comprising a material having isotopes intrinsically emitting radiation causing intrinsic scintillation events having an intensity measurable by the photon detectors, wherein the gamma ray detection system comprises a calibration module configured to execute a spatial calibration procedure based on measurements of a plurality of said intrinsic scintillation events output by the photon detectors, the spatial calibration procedure for determining spatial positions of scintillating events in the monolithic scintillator plate as a function of the outputs of the plurality of photon detectors.

2. The gamma ray detection system according to claim 1, wherein said scintillator plate comprises a scintillating material layer and radioactive material layer arranged on or adjacent a major surface of the scintillating material layer, said radioactive material layer constituting said material having isotopes intrinsically emitting radiation, or wherein said scintillator plate comprises a scintillating material synthetically doped with a radioactive material constituting said material having isotopes intrinsically emitting radiation, or wherein said scintillator plate comprises a scintillating crystal containing Lutetium and the calibration process uses intrinsic Lu-176 activity.

3. The gamma ray detection system claim 1, wherein the signal processing and control system comprises an energy filter configured to exclude photon detector measurement outputs above a pre-defined upper energy threshold, and optionally the energy filter is configured to exclude photon detector measurement outputs below a pre-defined lower energy threshold.

4. The system according to claim 3 wherein said pre-defined upper energy threshold is in a range from 200 keV to about 1200 keV.

5. The system according to claim 4 wherein said pre-defined upper energy threshold is in a range from 200 keV to about 400 keV.

6. The system according to claim 5 wherein said pre-defined upper energy threshold is in a range from 200 keV to 230 keV, for instance about 202 keV.

7. The system according to claim 4 wherein said pre-defined lower energy threshold is in a range from 0 keV to 90 keV.

8. The system according to claim 7 wherein said pre-defined lower energy threshold in a range from 20 keV to 90 keV.

9. The system according to claim 8 wherein said pre-defined lower energy threshold is in a range from 65 keV to 90 keV, for instance about 88 keV.

10. The gamma ray detection system according to claim 1, comprising at least two stacked scintillator plates, wherein the calibration procedure comprises measuring intrinsic scintillation events that are coincident between said at least two scintillator plates in order to select gamma rays with pre-defined energies of interest (e.g. 202 or 307 keV) emitted from one plate and absorbed in the other plate, and suppress the impact of a $\beta^-$ spectrum with unknown energy.

11. The gamma ray detection system according to claim 1, wherein the calibration module comprises an algorithm for computing a self-organizing map of a two-dimensional spatial position of intrinsic scintillation events in a scintillation plate.

12. The gamma ray detection system according to claim 1, wherein the calibration module comprises an algorithm for computing local variance-minimization to improve spatial resolution of the two-dimensional spatial position of intrinsic scintillation events near edges of the scintillator plate.

13. The gamma ray detection system according to claim 1, wherein a plurality of photon detectors are mounted against each of said edges configured to detect scintillation events in the scintillator plates from gamma rays incident on the major surfaces.

14. The gamma ray detection system according to claim 1, wherein the detection module assembly surrounds a target zone and comprises a gap or orifice for ion beam emission therethrough.

15. The gamma ray detection system according to claim 1, comprising at least three scintillator plates, wherein the calibration procedure comprises measuring intrinsic scintillation events that are coincident between said at least three scintillator plates in order to select three localized scintillation events, one of them including contribution from a beta decay electron.

16. An ion beam therapy system for ion beam irradiation of a zone of tissue, comprising a patient support, an ion beam emitter movable relative to the patient support about at least an axis of rotation, and a gamma ray detection system according to claim 1.

17. A method of calibrating a gamma ray detection system comprising a computation system including a signal processing and control system, a detection module assembly including at least one detection module configured for detecting gamma ray emissions from a target zone, each detection module comprising at least one monolithic scintillator plate having a major surface oriented to generally face the target zone and lateral minor surfaces defining edges of the scintillator layer, and a plurality of photon detectors coupled to edges of said at least one monolithic scintillator plate and connected to the signal processing and control system, the scintillator plate comprising a material having isotopes intrinsically emitting radiation causing intrinsic scintillation events having an intensity measurable by the photon detectors, wherein the method comprises detecting an intensity and time of a plurality of said intrinsic scintillation events by the plurality of photon detectors, transmitting values of said detected intensities and times of scintillation events output by the plurality of photon detectors to a computing system, and executing a calibration module program in the computing system to determine spatial positions of scintillating events in the monolithic scintillator plate as a function of the outputs of the photon detectors.

18. The method according to claim 17 wherein detected intensities above a pre-defined upper energy level are excluded, and optionally detected intensities below a pre-defined lower energy level are excluded.

19. The method according to claim 18 wherein said pre-defined upper energy threshold is in a range from 200 keV to 1200 keV.

20. The method according to claim 19 wherein said pre-defined upper energy threshold is in a range from 200 keV to 400 keV.

21. The method according to claim 20 wherein said pre-defined upper energy threshold is in a range from 200 keV to 230 keV.

22. The method according to claim 19 wherein said pre-defined lower energy threshold is in a range from 0 keV to 90 keV.

23. The method according to claim 22 wherein said pre-defined lower energy threshold in a range from 20 keV to 90 keV.

24. The method according to claim 23 wherein said pre-defined lower energy threshold is in a range from 65 keV to 90 keV.

25. The method according to claim 17, wherein a self-organizing map of a two-dimensional spatial position of intrinsic scintillation events in a monolithic scintillator plate is computed by an algorithm of the calibration module.

26. The method according to claim 17, wherein a local variance-minimization to improve spatial resolution of the two-dimensional spatial position of intrinsic scintillation events near edges of the scintillator plate is computed by an algorithm of the calibration module.

27. The method according to claim 17 comprising measuring intrinsic scintillation events that are coincident between said at least two scintillator plates in order to select gamma rays with pre-defined energies of interest (e.g. 202 or 307 keV) emitted from one plate and absorbed in the other plate, and suppress the impact of $a_f$ spectrum with unknown energy.

28. The method according to claim 17 comprising measuring intrinsic scintillation events that are coincident between said at least three scintillator plates in order to select three localized scintillation events, one of them including contribution from a beta decay electron.

* * * * *